US009815222B2

(12) United States Patent
James et al.

(10) Patent No.: US 9,815,222 B2
(45) Date of Patent: Nov. 14, 2017

(54) PROCESS FOR THE PREPARATION OF A METAL-ORGANIC COMPOUND

(71) Applicant: The Queen's University of Belfast, Belfast (GB)

(72) Inventors: Stuart James, Belfast (GB); Tony McNally, Belfast (GB); Robert Haydon, Belfast (GB)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 14/888,466

(22) PCT Filed: May 27, 2014

(86) PCT No.: PCT/GB2014/051605
§ 371 (c)(1),
(2) Date: Nov. 2, 2015

(87) PCT Pub. No.: WO2014/191725
PCT Pub. Date: Dec. 4, 2014

(65) Prior Publication Data
US 2016/0176070 A1     Jun. 23, 2016

(30) Foreign Application Priority Data

May 27, 2013  (GB) .................................. 1309458.6

(51) Int. Cl.
| C07F 3/06 | (2006.01) |
| C07F 3/00 | (2006.01) |
| B29B 7/00 | (2006.01) |
| C07F 15/06 | (2006.01) |
| C07F 1/08 | (2006.01) |
| C07F 3/02 | (2006.01) |
| C07F 5/06 | (2006.01) |
| C07F 15/04 | (2006.01) |
| B01J 20/22 | (2006.01) |
| B01J 20/30 | (2006.01) |
| B01J 20/28 | (2006.01) |

(52) U.S. Cl.
CPC ............. *B29B 7/005* (2013.01); *B01J 20/226* (2013.01); *B01J 20/28042* (2013.01); *B01J 20/3007* (2013.01); *B01J 20/3085* (2013.01); *C07F 1/08* (2013.01); *C07F 3/02* (2013.01); *C07F 3/06* (2013.01); *C07F 5/06* (2013.01); *C07F 5/069* (2013.01); *C07F 15/04* (2013.01); *C07F 15/06* (2013.01)

(58) Field of Classification Search
CPC ....................................................... C07F 3/06
USPC ................................................ 548/101, 107
See application file for complete search history.

(56) References Cited

U.S. PATENT DOCUMENTS 8,466,285 B2 * 6/2013 James ................... C07C 51/418
502/151
2011/0177126 A1 7/2011 Sanz Herranz et al.

FOREIGN PATENT DOCUMENTS

WO    WO-2007023295 A2    3/2007

OTHER PUBLICATIONS

Jeanjean, Fabien, "International Search Report," prepared for PCT/GB2014/051605, dated Jul. 25, 2014, four pages.
Kathuria, Ajay, et al.; "Deterioration of Metal-Organic Framework Crystal Structure During Fabrication of poly(L-lactic acid) Mixed-Matrix Membranes"; Polym Int, vol. 62; Feb. 25, 2013; pp. 1144-1151.
Pichon, Anne, et al.; "Solvent-Free Synthesis of a Microporous Metal-Organic Framework"; CrystEngComm, Royal Society of Chemistry, vol. 8; Feb. 6, 2006; pp. 211-214.
Beldon, Patrick J., et al.; "Rapid Room-Temperature Synthesis of Zeolitic Imidazolate Frameworks by Using Mechanochemistry"; Angewandt Chemie International Edition, vol. 49, No. 50; Dec. 10, 2010; pp. 9640-9643.
Chapman, Mary E., et al.; "Synthesis, X-Ray Structures, and Magnetic Properties of Copper(II) Pyridinecarboxylate Coordination Networks"; Crystal Growth & Design, ACS, vol. 1, No. 2; Jan. 1, 2001, pp. 159-163.
Garay, Ana Lazuen, et al.; "Solvent-Free Synthesis of Metal Complexes"; Chem. Soc. Rev., vol. 36; Feb. 19, 2007; pp. 846-855.
Timms, Peter L.; "New Developments in Making Compounds and Materials by Condensing Gaseous High-Temperature Species at Atmospheric or Low Pressure"; Chemical Society Reviews; Jan. 1, 1996; pp. 93-99.
Filatov, Alexander S., et al.; "Gas-Phase Assembling of Dirhodium Units into a Novel Organometallic Ladder: Structural and DFT Study"; Crystal Growth & Design, vol. 6, No. 6; May 6, 2006; pp. 1479-1484.
Bala, Muhammad D., et al.; "Organometallic Chemistry in the Melt Phase"; Journal of Organometallic Chemistry, vol. 692; Oct. 27, 2006; pp. 709-730.

(Continued)

*Primary Examiner* — Charanjit Aulakh
(74) *Attorney, Agent, or Firm* — Winstead PC

(57) ABSTRACT

A process for the preparation of a metal-organic compound, said metal-organic compound comprising at least one metal ion and at least one organic ligand, wherein said organic ligand is capable of associating with said metal ion, comprising at least the steps of; providing a first reactant comprising at least one metal in ionic form; providing a second reactant comprising at least one organic ligand capable of associating with said metal in ionic form; and admixing said first and second reactants under conditions of prolonged and sustained pressure and shear sufficient to synthesize said metal-organic compound.

23 Claims, 17 Drawing Sheets

(56) References Cited

OTHER PUBLICATIONS

James, Stuart L.; "Metal-Organic Frameworks"; Chem. Soc. Rev., vol. 32; Jun. 27, 2003; pp. 276-288.

Meek, Scott T., et al.; "Metal-Organic Frameworks: A Rapidly Growing Class of Versatile Nanoporous Materials"; Adv. Mater., vol. 23; Oct. 22, 2010; pp. 249-267.

Long, Jeffrey R., et al.; "The Pervasive Chemistry of Metal-Organic Frameworks"; Chem. Soc. Rev., vol. 38; Apr. 1, 2009; pp. 1213-1214.

Murray, Leslie J., et al.; "Hydrogen Storage in Metal-Organic Frameworks"; Chem. Soc. Rev., vol. 38; Mar. 25, 2009; pp. 1294-1314.

Chui, Stephen S.-Y., et al.; "A Chemically Functionalizable Nanoporous Material $[Cu_3(TMA)_2(H_2O)_3]_n$"; Science, vol. 283; Feb. 19, 1999; pp. 1148-1150.

Park, Kyo Sung, et al.; "Exceptional Chemical and Thermal Stability of Zeolitic Imidazolate Frameworks"; PNAS, vol. 103, No. 27; Jul. 5, 2006; pp. 10186-10191.

Chen, Banglin, et al.; "Interwoven Metal-Organic Framework on a Periodic Minimal Surface with Extra-Large Pores"; Science, vol. 291; Feb. 9, 2001; pp. 1021-1023.

Manas-Zloczower, Ica; "Analysis of Mixing in Polymer Processing Equipment"; Rheology Bulletin, vol. 66, No. 1; Jan. 1997; 4 pages.

\* cited by examiner

PROCESS FOR THE PREPARATION OF A METAL-ORGANIC COMPOUND

The present invention relates to processes for preparing metal-organic compounds, the compounds obtained in this way and their use.

Metal-organic compounds are those which consist of one or more metal ions with one or more organic groups chemically bonded to the metal ions. They are variously termed organometallic compounds, coordination compounds, coordination complexes and metal complexes. The organic groups attached to the metal are often termed 'ligands'. Typically, the organic group bonds to the metal ion through an atom of carbon, nitrogen, oxygen, silicon, phosphorus or sulphur, although they may also bind through atoms of arsenic or selenium. The descriptor 'organometallic' is normally reserved for the subset of such compounds in which the organic group is bonded to the metal ion through a carbon atom.

Metal organic compounds are well documented as a substantial and well-recognised class of chemical compounds in standard chemistry text books such as *Inorganic Chemistry* (Housecroft and Sharpe, Pearson Education Limited, Edinburgh, first edition 2001), *Inorganic Chemistry* (Shriver and Atkins, Oxford University Press, Oxford, fourth edition, 2006) and in major reference works such as *Comprehensive Coordination Chemistry II*, ed. J. A. McCleverty and T. J. Meyer, Elsevier, 2004 and *Comprehensive Organometallic Chemistry II*, ed. E. W. Abel, F. G. A. Stone and G. Wilkinson, Elsevier, 1995.

All metal ions may form metal-organic complexes. Illustrative examples include: $Li^+$, $Na^+$, $K^+$, $Mg^{2+}$, $Ca^{2+}$, $Sr^+$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Cr^{4+}$, $Cr^{6+}$, $Mo^{3+}$, $Mo^{6+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pd^{4+}$, $Pt^{2+}$, $Pt^+$, $Pt^{4+}$, $Cu^{2+}$, $Cu^+$, $Ag^+$, $Au^+$, $Au^{3+}$, $Zn^{2+}$, $Cd^{2+}$, $Hg^{2+}$, $Al^{3+}$, $Ga^{3+}$, $In^{3+}$, $Ti^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$ and $Bi^+$, as well as lanthanide ions such as $La^{3+}$, $Ce^{3+}$, $Ce^{4+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$ and actinide ions such as $Th^{3+}$, $Pa^{3+}$, $U^{3+}$, $U^{6+}$, $Np^{3+}$, $Pu^{3+}$, $Am^{3+}$, $Cm^{3+}$, $Bk^{3+}$, $Cf^{3+}$, $Es^{3+}$, $Fm^{3+}$, $Md^{3+}$, $No^{3+}$ and $Lr^{3+}$.

Methods which are used for the synthesis of such compounds normally involve the use of appropriate solvents to dissolve, or partially dissolve one or both the metal-containing reactant and the reactant which provides the organic group. The solvent is normally present in a very large excess. The use of such solvent-based methods increases the technical complexity, time and cost of the synthesis. There may also be environmental contamination from the use of such solvents on large scales such as in industrial processes. Many organic solvents are toxic and/or harmful to the environment. Thus it is very desirable to synthesise metal organic compounds in the absence of solvent. Solvent-free methods of synthesis are relatively undeveloped but include grinding together the solid reactants using, for example, a mortar and pestle or a ball mill (A. L. Garay, A. Pichon and S. L. James Chem. Soc. Rev., 2007, 36, 846). Alternatively, solvent-free synthesis may be achieved by causing one or both of the reactants to be in the gas phase (P. L. Timms, *Chem. Soc. Rev.*, 1996, 93; A. S. Filatov, A. Y. Rogachev and M. A. Petrukhina, *Cryst. Growth Des.*, 2006, 6, 1479). Alternatively, one or both reactants may be induced to melt (M. D. Bala, N. J. Coville J. Organomet. Chem. 2007, 692, 709). However, solvent-free methods which operate on a continuous basis, rather than in batch mode, and which can be readily scaled-up for the synthesis of larger amounts of product, are still desired.

A subset of metal organic compounds is termed 'metal-organic frameworks' (MOFs).

Metal-organic frameworks are crystalline or non-crystalline, porous metal-organic compounds, having particular pores or pore distributions and large specific surface areas. In recent times they have in particular become the object of comprehensive research work. Applications include catalysis or separating, storing and releasing a variety of chemical compounds and gasses.

Metal-organic frameworks are well-known in the art and have been given various names in the literature, including coordination polymers, metal-organic coordination networks (MOCNs) and porous coordination polymers (PCPs).

In MOFs, the organic groups bridge between metal ions so that a polymeric structure results. This polymeric network may extend in one, two or three dimensions. Of particular interest are those which extended in two or three dimensions since such structures may be porous. Specifically, they may contain pores which can accommodate other molecules. When other molecules are absorbed into the pores, the metal-organic framework may be described as a host and the absorbed molecules may be described as guests. Absorption of the guests into the pores may occur by simple exposure of the MOF to the guests when the guests are in liquid or gaseous form such that they can diffuse into the porous structure. Because the pores have specific sizes, shapes and chemical functionalities such materials can show selectivity for the absorption of particular guests. The property of porosity thus gives rise to potential applications such as those which require storage, separation or release of the guest species. For example, liquids or gases may be stored in such materials, mixtures of gases may be separated into their components using such materials, mixtures of liquids may be separated into their components using such materials, and guests may be released by such materials. In addition, such materials may function as catalysts by facilitating chemical changes in the guests, or as sensors for the guests through a guest-induced change in one or more of the physical properties of the MOF.

General information on different known MOFs and conventional synthesis methods are reported in a number of publications, including, "Metal-organic frameworks," James, S. L., Chemical Society Reviews 32 (2003) 276-288; "Metal-Organic Frameworks: A Rapidly Growing Class of Versatile Nanoporous Materials," Meek, S. T. et al., Advanced Materials 23 (2011) 249-267; Long, J. (ed.) Chemical Society Reviews, Metal Organic Frameworks theme issue, 2009, vol. 38. Chui et al., Science 283 (1999), 1148-1150, describe, for example, the preparation of the Cu-BTC MOF (also known as HKUST-1), in which a copper salt, viz. copper nitrate trihydrate is used as starting material and this salt and trimesic acid ($H_3BTC$) are dissolved in a solvent mixture of water and ethanol to synthesize the MOF material. Here the ratio of the mass of the solvent to that of the reactants was 1664%.

Park et al., Proceedings of the National Academy of Science 27 (2006) 10186-10191, describe, for example, the preparation of the MOF ZIF-8, in which a zinc salt (zinc nitrate) is used as starting material and this salt and 2-methylimidazole (H-MeIM) are dissolved in the solvent N,N'-dimethylformamide (DMF) to synthesize the MOF. Here the ratio of the mass of the solvent to that of the reactants was 6320%.

Chen et al., Science 291 (2001), 1021-1023, describe, for example, the preparation of an MOF-14, in which a copper salt (copper nitrate) is used as starting material and this salt and 4,4',4"-benzene-1,3,5-triyltribenzoic acid (H3BTC) are dissolved in a solvent mixture of N,N'-dimethylformamide (DMF), ethanol and water to synthesize the MOF. Here the ratio of the mass of the solvent to that of the reactants was 2444%.

As described in the references above, numerous methods have been developed for synthesizing MOFs using precursors including a metal precursor and corresponding organic ligand. However, most require the use of one or more solvents and heat. The yield obtained using these methods is reasonable for laboratory use, but they are inefficient on an industrial scale in terms of time, separation of additional material (e.g. solvents), and heating, and further suffer from the requirement for environmentally unfriendly solvent use.

Synthesis can be described as the process of forming the chemical bonds which hold together the framework structure of the material. After synthesis, microporous materials such as metal organic frameworks typically contain molecules within their pores, such as solvent molecules or by-products of the synthesis. Therefore, such materials typically require a process known as activation to remove these species so that the pores are rendered empty and available to sorbates of interest. Activation typically consists of heating or subjecting to reduced pressure or washing with another solvent, or any combination of such procedures. These methods are well known in the art and do not constitute part of the actual synthesis of the material. Thus, these processes may also be required to activate the materials as prepared by the methods described in this patent.

Reduced solvent or solvent-free synthesis of such metal-organic metallic frameworks is desired. WO 2007/023295A2 (incorporated herein in its entirety) describes a process for the preparation of metal-organic frameworks by grinding, such as in a ball mill, wholly or substantially in the absence of solvent. However, a continuous production process is required to increase the yield of product that can be produced in industrial production.

In the following discussion, the term "metal organic compound" encompasses porous, crystalline metal-organic frameworks as a subset.

In recent times the potential of extrusion has begun to be realised in pharmaceutical synthesis applications. US 2011/0177126A describes a method of producing co-crystals by exposing a mixture of two co-crystal precursors to prolonged and sustained conditions of pressure and shear, preferably in an extrusion process. However, such co-crystals are only held together by non-covalent forces, i.e. low binding energy.

One object of the present invention is to provide a continuous process for the production of metal-organic compounds, which is also capable of providing an economical yield, and with increased efficiency in terms of materials, time, cost or energy, compared to the solvent-based methods, whilst also being environmentally friendly.

Thus, the present invention provides a method of producing a metal-organic compound, the method comprising the steps of:

Providing a first reactant which includes at least one metal in ionic form, and a second reactant which includes at least one at least monodentate organic ligand, mixing said first and second reactants together; and exposing the mixture of said first and second reactants to prolonged and sustained conditions of pressure and shear sufficient to form a metal-organic compound.

The present inventors have surprisingly found that the metal-organic compounds, only disclosed in the prior art as requiring solvent-based formation, can now be formed by a process based only on mixing the selected metal ion(s) and organic ligand(s) together and exposing said mixture to conditions of pressure and shear to form covalent bonds. In this way, the metal-organic compounds can be formed without utilising a conventional solvothermal process. Unlike prior art methods, at no point during the process of the invention is a clear liquid phase observed.

This may be achieved wholly or substantially in the absence of solvent, and may preferably be carried out by subjecting the components to an extrusion process.

Widespread industrial use of extruders has conventionally been in the plastics, rubber and food industries. Most conventional polymer processing machinery can be adapted for use in a Good Manufacturing Practices (GMP) environment. Extrusion processing operations can be readily scaled from the laboratory to manufacturing scale.

The process of the present disclosure is also suitable for use with the same combinations of metals in ionic form and organic ligands as used in conventional solvent-based processes known in the art, for example as discussed above.

The inventors have surprisingly found that the transformations achievable according to the invention are possible in very brief residence times, from as little as a few seconds to 40 minutes. It is preferred that the first and second reactants are exposed to sustained conditions of pressure and shear for at least 1 minute, preferably 2 minutes or longer, particularly 2 to 40 minutes, especially from 2 to 30 minutes. It will be appreciated that the length of time required to form the metal organic compound will generally depend on the severity of the pressure and shear conditions to which the first and second substances are exposed, but it has been found that prolonged and sustained exposure typically results in improved metal-organic compound formation. However, in many instances there will be a balance between possible degradation of the organic ligand though excessive time spent under shear and pressure conditions, against the amount of time required for metal-organic compound formation. In addition, for the formation of metal-organic frameworks, over-exposure to high shear and/or high temperature may reduce or remove the crystallinity of the material. Such a balance depends on the materials used and the conditions imposed on these materials and can be determined by the person skilled in the art.

In a preferred embodiment the pressure and shear are applied in an extrusion method. It is surprising that the process of extrusion can be used to obtain metal organic compounds, including crystalline and non-crystalline, porous metal-organic frameworks. In addition, extrusion provides a method of producing high yields of metal-organic compounds, and in large quantities. This provides very significant advantages over existing metal-organic compound synthesis techniques. Surprisingly, it has been found that extrusion can bring about quantitative and highly precise chemical transformations (i.e. to give a single crystalline phase) involving breaking and forming strong chemicals bonds such as those between Al and O (typically ca. 450 kJ/mol), while preserving high crystallinity in the resulting product, i.e. one could expect that that the conditions of pressure and shear exerted on the reactants would break down the long range order in the material, rendering it amorphous. The inventors have surprisingly found that this is not the case.

By extrusion is meant the conveyance of the substances through an elongate lumen, while pressure and shear are applied; typically the pressure and shear are applied at least partially by means which conveys the substances through the lumen. The extrusion may also involve passing the substances through a die to shape or otherwise manipulate the product of the extrusion process, although this is generally not necessary for metal-organic compound formation.

It is generally preferred that the extrusion is a screw based extrusion method. Although single screw extrusion may be suitable in some embodiments, it is generally preferred that the method is a screw-based extrusion method wherein two or more screws interact with the mixture of said first and second reactants during the extrusion process. Such methods provide for a greater degree of mixing and otherwise manipulating the mixture to obtain the desired metal-organic compound.

In a preferred embodiment the screw-based extrusion method is a twin-screw extrusion method. Twin-screw methods provide a useful balance of minimising complexity of the extrusion apparatus, while providing the ability to manipulate the extrusion process as desired. It is, of course, possible that an extrusion process in which three or more screws interact may be used and such systems are well known for the extrusion of polymers.

It is generally preferred that, where a twin-screw extrusion method is used, it is a co-rotating method. However, in some embodiments it may be found that a counter-rotating method provides some benefits.

Counter-rotating screws are used when very high shear is required, as they produce high pressures and shear forces between the two counter rotating screws. Thus counter-rotating screws may be useful where a very high level of shear and pressure is preferred to form the metal-organic compounds. However, counter-rotating screw systems can suffer from problems with air entrapment, low maximum screw speeds and output; these may be disadvantages in certain applications.

Co-rotating systems can achieve a good level of mixing and conveying of materials and can also be operated at high speeds and thus achieve high output rates. They are less prone to wear than counter-rotating systems.

It is preferred, where more than one screw is present, that the screws are at least substantially intermeshing, preferably fully intermeshing. A pair of screws can be considered to be fully intermeshing when the flight tip of helical threaded regions of each screw substantially reaches the root of the other screw; there will typically be a small gap to provide mechanical clearance, but generally the gap will be kept to a minimum. In an effort to quantify this term, it could be suggested that a pair of screws are substantially intermeshing when the gap between the flight tip of one screw and the root of the other is 10% or less of the total depth of the root of the screws, more preferably 5% or less. Intermeshing systems have the advantage that they are self-wiping and prevent localised overheating of materials within the system.

Of course, it should be noted that, in certain embodiments of the present invention, it may be preferable to use a non-intermeshing system. Non-intermeshing systems may be used where it is desired that large amounts of volatiles are removed from the system, or where highly viscous materials may result in unacceptably high levels of torque being applied to the system.

Another potential type of extruder for use in the present method is a recirculating extruder. Recycling extruders are typically twin-screw systems in which a batch of material can be processed for a predetermined period until being discharged from the system. Such extruders, for example the Haake Minilab, may be useful in a variety of applications, though are not as widely used as more conventional non-recirculating extruders.

It is generally preferred that the method is performed solely with the first and second reactants which are capable of forming a metal organic compound, as would be known by someone skilled in the art.

(i) First Reactant

The first reactant may be a salt, or in salt form, such as a nitrate, nitrite, sulfate, hydrogen sulphate, oxide, halide, acetate, oxide, hydroxide, benzoate, alkoxide, carbonate, acetylacetonate, hydrogen carbonate, fluoride, chloride, bromide, ionided, phosphate, hydrogen phosphate, dihydrogen phosphate, or the like.

Suitable metal ions include: $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$ $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Ti^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $Bi^{3+}$ and $Bi^{+}$ can be mentioned in particular. Particularly preferred are $Cu^{2+}$, $Cu^{+}$, $Fe^{2+}$, $Fe^{3+}$, $Zn^{2+}$, $Co^{3+}$, $Co^{2+}$ and $Mg^{2+}$. Especially preferred are $Cu^{2+}$, $Cu^{+}$ and $Zn^{2+}$. However, others may also be contemplated by those skilled in the art.

(ii) Second Reactant for Metal Organic Compounds

The second reactant organic group may bind to the metal through one or more atoms. If binding through one atom they are termed monodentate. Examples of monodentate organic ligands include pyridines, imidazoles, imidazolates, nitriles, tertiary amines, secondary amines, primary amines, amides, tertiary phosphines, secondary phosphines, primary phosphines, thioethers, thiolates, ethers, alcohols, carboxylates, alkoxides, aryloxides and the like. A wide variety of functional groups may be present on such ligands which do not bind to the metal but which impart various properties such as desirable solubilities, optical properties, electronic properties etc, or which affect the characteristics of the chemical bond between the metal and the organic group. In the latter case these could for example be electron donating or electron withdrawing groups. The substituents may also impart desirable steric properties. The ligands may also be chiral. In addition to monodentate ligands, ligands may bind through more than on atom to the same metal. In such cases the ligands are known as chelates. If binding through two atoms they are termed bidentate chelates, if binding through three they are termed tridentate chelates etc. Any combination of the above types of binding groups may occur within a chelate ligand. Thus, important examples of chelates include 2,2'-bipyridine which binds through two pyridine groups, but also 8-quinolinate which binds through one N and one O atom. Further examples of bidentate organic ligands include diphosphines such as BINAP. Important tridentate ligands include terpyridine. Higher denticities are also common and an example of a hexadentate ligand is ethylenediaminetetraacetate (EDTA). The organic ligands may also take the form of a large ring inside which the metal ion is bonded to more than one atom of the ligand. Such ligands are termed macrocycles and important examples are porphyrins, phthalocyanines, tetraamines such as cyclam and cyclic polyethers such as crown ethers, including for example 15-crown-5, 18-crown-6 and the like. The ligand may also take the form of a cage inside which the metal ion is bound to more than one atom of the ligand. Such ligands may be referred to as cryptands and are well known in the art.

These reactions may be thought of in terms of acid-base reactions. In particular if the organic ligand is added in the form of a carboxylic acid it can be regarded as a Brønsted acid which donates a proton to the basic anions of the metal salt (for example the hydroxide ions of a metal hydroxide, or the oxide dianions of a metal oxide) to give the metal salt of the carboxylic acid. Water is formed as a byproduct in that particular case. Ligands which are added in the form of sulphonic acids, imidazoles and phosphonic acids may be thought of acting as Brønsted acids in a similar way to carboxylic acids.

Alternatively, if the ligand is intended to bind to the metal ion through an amine or pyridine functional group, which would not contain an proton which is easily lost, the ligand may be regarded as a Lewis base which donates a pair of electrons toward the Lewis acidic metal ion of the metal salt reactant to give a product which is Lewis acid-Lewis base adduct or complex.

In such terms it can be understood that these reactions are generally thermodynamically favourable, but they are normally far too slow to occur between two solid reactants to be practically useful. Thus, such reactions are conventionally done in solution, requiring a large excess of solvent, or, as revealed here, by grinding together the solid reactants to induce sufficient shear and mixing of the solid reactants.

(iii) Second Reactant for Metal Organic Frameworks

For the case of metal organic frameworks, the second reactant includes at least one at least bidentate organic bridging ligand.

The term "at least bidentate organic compound" as used within the scope of the present invention refers to an organic compound comprising at least one functional group which is able to form at least two, preferably two coordinative bonds to a given metal ion and/or to form one coordinative bond each to two or more, preferably two metal atoms.

Examples of functional groups to be mentioned, via which the said coordinative bonds can be formed, include the following functional groups in particular: —$CO_2H$, —$SO_3H$, —$Si(OH)_3$, —$PO_3H$, —CN, —$NH_2$, —NHR or —$NR_2$. Two or more such groups may be attached to an organic group, R', which, for example, is preferably an alkylene group having 1, 2, 3, 4 or 5 carbon atoms such as eg a methylene, ethylene, n-propylene, i-propylene, n-butylene, i-butylene, t-butylene or n-pentylene group or an aryl group containing one or two aromatic nuclei such as e.g. two $C_6$ rings which may or may not be condensed and, independently of one another, can be substituted in a suitable manner by at least one substituent each, and/or which, independently of one another, can each contain at least one heteroatom such as e.g. N, O and/or S. The at least two functional groups can in principle be bound to any suitable organic compound, as long as there is the assurance that the organic compound having these functional groups is capable of forming the coordinative bond and of producing the framework material.

The organic compounds comprising the at least two functional groups are preferably derived from a saturated or unsaturated aliphatic compound or an aromatic compound or a compound which is both aliphatic and aromatic.

The aliphatic compound or the aliphatic moiety of the both aromatic and aliphatic compound can be linear and/or branched and/or cyclic, a plurality of cycles per compound also being possible. More preferably, the aliphatic compound or the aliphatic moiety of the both aliphatic and aromatic compound comprises from 1 to 15, more preferably from 1 to 14, more preferably from 1 to 13, more preferably from 1 to 12, more preferably from 1 to 11 and particularly preferably from 1 to 10 C atoms such as e.g. 1, 2, 3, 4, 5, 6, 7, 8, 9 or 10 C atoms. Particularly preferred in this context are, inter alia, methane, adamantane, acetylene, ethylene butadiene or benzene.

The aromatic compound or the aromatic moiety of the both aromatic and aliphatic compound can have one or alternatively more nuclei such as e.g. 2, 3, 4 or 5 nuclei, with the option of the nuclei being separate and/or at least two nuclei being present in condensed form. Particularly preferably, the aromatic compound or the aromatic moiety of the both aliphatic and aromatic compound has 1, 2 or 3 nuclei, one or two nuclei being especially preferred. Independently of one another, each nucleus of the above mentioned compound may further comprise at least one heteroatom such as e.g. N, O, S, B, P, Si, Al, preferably N, O and/or S. More preferably, the aromatic compound or the aromatic moiety of the both aromatic and aliphatic compound comprises one or two $C_6$ nuclei, the two nuclei being either separate or being present in condensed form. Aromatic compounds to be mentioned in particular are imidazolate, benzene, naphthalene and/or biphenyl and/or bipyridyl and/or pyridine.

Examples to be mentioned within the scope of the present invention of imidazole-based ligands are imidazole, 2-methylimidazole, 2-ethylimidazole and benzimidazole.

Examples to be mentioned within the scope of the present invention:

(a) of dicarboxylic acids are 1,4-butanedicarboxylic acid, tartaric acid, glutaric acid, oxalic acid, 4-oxo-pyran-2, 6-dicarboxylic acid, 1,6-hexanedicarboxylic acid, decane dicarboxylic acid, 1,8-heptadecane dicarboxylic acid, 1,9-heptadecanedicarboxylic acid, heptadecanedicarboxylic acid, acetylene dicarboxylic acid, 1,2-benzenedicarboxylic acid, 2,3-pyridinedicarboxylic acid, 2,3-pyridine-dicarboxylic acid, 1,3-butadiene-1,4-dicarboxylic acid, 1,4-benzenedicarboxylic acid, 1,3-benzenedicarboxylic acid, imidazole-2,4-dicarboxylic acid, 2-methyl-quinoline-3,4-dicarboxylic acid, quinoline-2,4-dicarboxylic acid, quinoxaline-2,3-dicarboxylic acid, 6-chloroquinoxaline-2,3-dicarboxylic acid, 4,4l-diaminphenylmethan-3,3'-dicarboxylic acid, quinoline-3,4-dicarboxylic acid, 7-chloro-4-hydroxyquinoline-2,8-dicarboxylic acid, diimiddi-carboxylic acid, pyridine-2,6-dicarboxylic acid, 2-methylimidazole-4,5-dicarboxylic acid, thiophene-3,4-dicarboxylic acid, 2-isopropyl-4,5-dicarboxylic acid, tetrahydropyrane-4,4-dicarboxylic acid, perylene-3,9-dicarboxylic acid, perylenedicarboxylic, pluriol E 200-dicarboxylic acid, 3,6-dioxaoctanedicarboxylic acid, 3,5-cyclohexadiene-1,2-dicarboxylic acid, octanecarboxylic acid, pentane-3,3-carboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis-(phenylamino)-benzene-2,5-dicarboxylic acid, 1-1'dinaphthyl-8,8'-dicarboxylic acid, 7-chloro-8-methylquinoline-2,3-dicarboxylic acid, 1-anilinoanthraquinone-2,4'-dicarboxylic acid, polytetrahydrofuran-250-dicarboxylic acid, 1,4-bis-(carboxymethyl)-piperazin-2,3-dicarboxylic acid, 7-chloroquinoline-3, 8-dicarboxylic acid, 1-(4-carboxy)-phenyl-3-(4-chloro)-phenyl-pyrazolin-4,5-dicarboxylic acid, 1,4, 5,6,7,7-hexachloro-5-norbornene-2,3-dicarboxylic acid, phenylindanedicarboxylic acid, 1,3-dibenzyl-2-oxo-imidazolidine-4,5-dicarboxylic acid, 1,4-cyclohexanedicarboxylic acid, naphthalene-1,8-dicarboxylic acid, 2-Benzoylbenzol-1,3-dicarboxylic acid, 1,3-dibenzyl-2-oxo-imidazolidine-4,5-cis-dicarboxylic acid, 2,2'-biquinoline-4, 4'-di-carboxylic acid, pyridine-3,4-dicarboxylic acid, 3,6,9-trioxaundecanedicarboxylic acid, 0-hydroxy-benzophenone-dicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazine dicarboxylic acid, 4,4'-diaminodiphenyl ether-diimidedicarboxylic acid, 4,4'-diaminodiphenylmethanediimidedicarboxylic acid, 4,4'-diamino-diphenylsulfone diimidedicarboxylic acid, 2,6-naphthalene dicarboxylic acid, 1,3-adamantanedicarboxylic, 1,8-naphthalenedicarboxylic acid, 2,3-naphthalenedicarboxylic acid, 8-Methoxy-2, 3-naphthalenedicarboxylic acid, 8-nitro-2, 3-naphthoic acid, 8-sulfo-2,3naphthalindicarboxylic acid, anthracene-2,3-dicarboxylic acid, 2',3'-diphenyl-p-terphenyl4,4'-dicarboxylic acid, diphenyl-4,4'-dicarboxylic acid, imidazole-4,5-dicarboxylic acid, 4 (1H)-oxo-thiochromen-2, 8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontandicarboxylic acid, tetradecanedicarboxylic acid, 1,7-heptanedicarboxylic acid, 5-hydroxy-1,3-benzenedicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxy-diphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-Dichlorfluorubin-4, 11-dicarboxylic acid, 7-chloro-3-methylquinoline-6,8-dicarboxylic acid, 2,4-dichlorobenzophenone-2'5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecane, 5,6-dehydronorbornan-2,3-dicarboxylic acid or 5-ethyl-2,3-pyridinedicarboxylic acid, (b) of tricarboxylic acids are;
2-hydroxy-1,2,3-propanetricarboxylic acid, 7-chloro-2,3,8-quinolinetritri carboxylic acid, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propane, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurinetricarboxylic acid, (c) of tetratricarboxylic acids are:
1,1-dioxide-perylo[1,12-BCD]thiophene-3,4,9,10-tetracarboxylic acid, perylenetetracarboxylic acids such as perylene3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octanetetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofilrantetracarboxylic acid or cyclopentanetetracarboxylic acids such as cyclopentane-1,2,3,4-tetracarboxylic acid. Most especially preferred within the scope of the present invention is the use, where suitable, of at least monosubstituted mono-, di-, tri-, tetra- or polynuclear aromatic di, tri- or tetracarboxylic acids, each of the nuclei optionally comprising at least one heteroatom, where two or more nuclei may comprise identical or different heteroatoms. Preferred, for example, are mononuclear dicarboxylic acids, mononuclear tricarboxylic acids, mononuclear tetracarboxylic acids, dinuclear dicarboxylic acids, dinuclear tricarboxylic acids, dinuclear tetracarboxylic acids, trinuclear dicarboxylic acids, trinuclear tricarboxylic acids, trinuclear tetracarboxylic acids, tetranuclear dicarboxylic acids, tetranuclear tricarboxylic acids and/or tetranuclear tetracarboxylic acids. Examples of suitable heteroatoms are N, O, S, B, P, Si, Al, preferred heteroatoms in this context being N, S and/or O. Suitable substituents to be mentioned in this respect are, inter alia, —OH, a nitro group, an amino group or an alkyl or alkoxy group.

Accordingly, the present invention also relates to a method as described above, wherein the at least bidentate organic compound used is an aromatic di-, tri- and/or tetracarboxylic acid.

Particularly preferred at least bidentate organic compounds used in the method according to the invention are acetylenedicarboxylic acid (ADC), benzenedicarboxylic acids, naphthalenedicarboxylic acids, biphenyldicarboxylic acids such as e.g. 4,4'-biphenyldicarboxylic acid (BPDC), bipyridinedicarboxylic acids such as e.g. 2,2'-bipyridinedicarboxylic acids such as e.g. 2,2'-bipyridine-5,5'-dicarboxylic acid, benzenetricarboxylic acids such as e.g. 1,2,3-benzenetricarboxylic acid or 1,3,5-benzenetricarboxylic acid (BTC), adamantanetetracarboxylic acid (ATC), adamantanedibenzoate (ADB) benzenetribenzoate (BTB), methanetetrabenzoate (MTB), adamantanetetrabenzoate or dihydroxyterephthalic acids such as e.g. 2,5dihydroxyterephthalic acid (DHBDC).

Most especially preferred within the scope of the present invention is the use of, inter alia, terephthalic acid, 2,5-dihydroxyterephthalic acid, 1,2,3-benzenetricarboxylic acid, 1,3,5-benzenetricarboxylic acid or 2,2'-bipyridine-5,5'-dicarboxylic acid.

Further examples of metal-organic compounds able to be prepared by the present invention are listed in the accompanying Table 1.

Preferably, the process is a continuous process.

The first and second reactants may be mixed prior to passing into the extruder.

The extrusion process may be a dry extrusion process.

A liquid, optionally one or more liquids, which may or may not act as a solvent, is generally not required but can optionally be added. Such a liquid may be any substance, including organic solvents and water, which either is, or forms, or otherwise becomes, a liquid in situ, i.e. during the process of the present invention. Such a liquid may act as a lubricant more than a solvent, but still have some solvating ability. Hence, the process of the present invention is wholly or substantially in the absence of solvent, as any liquid added may unintentionally also be a solvent. A low or very low volume of a liquid (in proportion to the reactants, for example <500% wt, <400% wt, <200% wt, 100%, 75% or even <50%, or even <20% or <10% or even <5%), can therefore still be involved, but as an additive to assist the process which is proceeding due to the grinding action. In an embodiment, <500% wt is used.

It is also noted that one or more by-products of the process of the present invention may be a solvent or solvents, e.g. water or an organic acid such as acetic acid. Such by-products are not intended to be part of the process of the present invention.

It may be desirable that the mixture of said first and second substances is exposed to additional heat. By "additional heat" it is meant that the mixture has heat applied to it, beyond the ambient temperature and beyond the heat produced by friction during the extrusion process.

In certain embodiments it is preferred that the process is carried out, for at least a portion of the duration of the process, at a temperature which may induce some melting of the reactants and/or products. The increased fluidity resulting from this partial or complete melting may in some cases lead to enhanced reactivity, manifested for example in causing the reaction to occur, or enabling it to occur in a shorter time. In such cases the temperature reached may still be below that of a given individual reactant and melting may still occur since a mixture of several substances will often melt at lower temperatures than any of the components of the mixture in pure form.

In general it is preferred that the temperature is slightly below the melting point of the reactant with the lowest melting point, though it might be at or slightly above the melting point. In preferred embodiments the temperature may be within 20° C. of the melting point, preferably within 10° C. of the melting point. It has been found that where such a temperature is used, there is a benefit in terms of metal-organic compound formation.

Depending on the conditions of shear and pressure and dwell time required during the extrusion process to obtain metal-organic compounds of the desired properties and yield, the configuration of the screw or screws can be altered. In general twin screw or other multiple screw arrangements are more amenable to modification of configuration, but it is possible to a lesser extent with a single screw extruder. It is possible to alter the following aspects of the extrusion apparatus or process, amongst others: length of barrel, ratio of length:diameter of the barrel (L/D ratio), composition of the screw elements (e.g. dispersive or distributive mixing elements, forward or reverse feed elements, depth of screw root (i.e. thread depth), screw rotation speed, feeding method (starvation feed versus flood feeding), number of passes through the extruder. These aspects enable a high degree of control over the extrusion process and the resultant metal-organic compound product.

It has been found that during extrusion it is preferable that the L/D ratio is 15/1 or greater (i.e. length is 15× or greater than the diameter of the screw). Preferably the L/D ratio is 20/1 or greater, and in some embodiments a ratio of 30/1 or greater may be preferable. An L/D ratio of 40/1 has been found to be well suited to formation of metal-organic compounds. These ratios apply especially to twin-screw systems, but can also apply to other extrusion systems.

It is preferred that during extrusion the mixture is exposed to at least one period of distributive or dispersive mixing. It is generally preferable that the mixture is exposed to at least one period of dispersive mixing; dispersive mixing is more aggressive in terms of shear, pressure and heat production, and thus appears to often be useful in driving the formation of co-crystals. Generally it is most preferred that the mixture is exposed to at least one period of each of distributive and dispersive mixing.

The screw of an extruder, especially a twin-screw or other multiple screw extruder, can comprise a number of different elements which determine the conditions to which the substances are subjected during extrusion. It should be noted that these elements are not always "screws" in the strictest sense, in that they may not comprise a continuous helical thread, but the term screw is nonetheless used in relation to the assembly as a whole regardless of the composition. Generally a significant portion of the length of a screw will comprise helical threads, typically half or more of its length will comprise helical threads.

The elements which make up the screw are typically assembled onto a shaft to form the complete screw. The shaft typically has a cross-section which prevents rotation of the elements relative to the shaft, eg. polygonal, and in many instances hexagonal. Each element is typically quite short relative to the total length of the screw. It is most convenient to talk of the length of the elements in terms of proportion of the diameter of the screw of the extruder.

Helical screw elements are used to convey the substances through the extruder, and they confer a relatively low level of mixing and application of pressure and shear. The level of pressure and shear applied by such helical elements can be varied, for example, by varying the degree of intermeshing of such helical elements in a multiple screw extruder, and varying the depth and/or pitch of such elements. Different helical screw types may be present, for example forward conveying elements, discharge elements or reverse screw elements.

Where more intense mixing and application of shear and pressure are required, this can be achieved by using mixing elements, especially mixing paddles. Mixing paddles typically comprise lobed elements, e.g. elliptical or similar shaped elements, which do not comprise a helical thread. The paddles provided a curved flat mixing surface. In a twin screw extruder one or more corresponding pairs of lobed elements may be provided on each of the screws. The lobed element on one screw is arranged such that it is rotationally offset relative to the lobed element on the other screw, typically by 90° for bi-lobed (i.e. generally elliptical) paddles, such that when the elements rotate the mixing surfaces of the lobed elements are separated by a narrow gap, which may remain substantially constant during rotation due to the corresponding shapes of the pair of paddles, or might vary to some degree during rotation. Different degrees of offset may be used for tri-lobed, or other shapes of mixing elements as appropriate. The effect of such mixing paddles is that the mixture is smeared between the pair of paddles and is thus subjected to relatively intense mixing at high shear and pressure. In addition, the flat nature of the mixing surface means that forward conveyance is not strongly promoted and, as such, the mixture tends to dwell in such elements; forward conveyance of the mixture is primarily driven by pressure exerted by the upstream mixture being forced by upstream conveying elements, although, as discussed below, certain configurations of mixing elements can provide a degree of forward conveyance.

The degree of mixing and application of shear and pressure can be determined by the number and configuration of mixing elements. Distributive mixing is a term well known in the art of extrusion and can be defined as "distributive mixing is the process of spreading a minor component throughout a matrix in order to achieve good spatial distribution". Distributive mixing can be achieved by providing a sequence of pairs of mixing (e.g. lobed) elements, where each pair of mixing elements is rotationally offset relative to the preceding pair, i.e. at staggered angles. Generally subsequent mixing elements are offset in the same direction as the direction of the helical portion which provided forward conveyance. Typically the length of each mixing element (e.g. lobed element) will be up to 0.25× the diameter of the screw, preferably at least 0.125× the diameter of the screw; e.g. for a screw of diameter 16 mm, each element might have a length of 4 mm. Distributive mixing can be considered to be mixing predominantly by rearranging flow paths of the mixture of the substances; in essence the relative short length of each mixing element means that the mixture is churned between the mixing elements, and the level of highly constrained smearing is relatively low. The amount of rotational offset determines the amount of conveyance such a distributive mixing sequence provides, and to some extent the severity of the mixing. Where a pair is offset from the preceding pair by from around 10° to 45° (typically 30°) in the same direction as the helix on the feed screw, a significant degree of forward conveyance is provided; an offset of from around 46 to 65° (typically 60°) provides somewhat less conveyance; and an offset of from around 75° to 90° provided significantly less conveyance—an offset of 90° provides essentially no conveyance of the mixture.

Dispersive mixing is an intense form of mixing and provides a high level of shear and pressure to the mixture. Dispersive mixing is a term well known in the art of extrusion and can be defined as "dispersive mixing involves the reduction in size of a cohesive minor component such as clusters of solid particles or droplets of a liquid". Dispersive mixing can be achieved when the mixture is forced to pass through an elongate mixing region where it is compressed and smeared between mixing surfaces of mixing elements. Dispersive mixing can be provided by one or more mixing elements, e.g. bi-lobed elements, which provide an elongate region of mixing surface without any rotational offset; i.e. the elongated region of mixing surface may be provided by a pair of comparatively long mixing elements (one on each screw of a twin-screw system) with substantially no rotational offset, or there may be a plurality of sequential shorter mixing elements which have substantially no rotational offset between subsequent elements. For example, a region of 0.5× the diameter of the screw or greater in length comprising lobed mixing elements With no rotational offset will provide dispersive mixing. Conveniently a dispersive mixing zone can comprise two or more lobed elements which are not offset relative to one another, i.e. they provide a substantially continuous mixing surface. In essence the significant aspect of dispersive mixing is that at least a portion of mixture is constrained to pass through mixing elements between which the mixture is smeared and a high degree of pressure and shear is applied this can be achieved using mixing elements as discussed above.

However, it should be noted that the above distributive and dispersive mixing systems are illustrative of preferred systems for use in the present invention. Other methods of achieving distributive or dispersive mixing could be envisaged by the person skilled in the art. A discussion of dispersive and distributive mixing is provided in Rheology Bulletin Vol. 66, No. 1 (January 1997) "Analysis of Mixing in Polymer Processing Equipment" by Ica Manas-Zloczower.

It is preferred that the extrusion apparatus used in the present method comprises dispersive mixing regions (i.e. regions comprising mixing elements) for at least 1/40 of the total length of the screw, preferably at least 1/30, more preferably at least 1/20 of the total length of the screw. Preferably there is at least one region of dispersive mixing, the region being at least 0.5 diameters in length. More preferably there is at least one region of dispersive mixing, and the total length of all the regions of dispersive mixing is at least 1.5 diameters or more, preferably 2 diameters or more.

In embodiments of the present invention it is preferred to have both mixing and dispersive mixing regions, i.e. regions comprising mixing elements. In a preferred embodiment the configuration comprises at least one region of distributive mixing followed by at least one region of dispersive mixing. In a preferred embodiment of the invention, at least two regions of distributive mixing and at least two regions of dispersive mixing are provided. It is preferred that each of the regions of distributive mixing are at least 1 diameter in length, more preferably at least 1.5 diameters in length, and they may be 2 or more diameters in length. It is preferred that each of the regions of dispersive mixing is at least 0.5 diameters in length, they may be 1 or more diameters in length, and they may be 1.5 or more diameters in length. Generally it is preferred that there is a total of 5 or more diameters in length of mixing regions, more preferably 10 or more diameters of mixing regions.

It is generally preferred that half of the total screw length or less of the extrusion system comprises mixing elements, more typically ⅖ or less, or ¼ or less of the total screw length comprises mixing elements. Of course the actual proportion may vary depending on the total screw length, and situations where more than half the total length comprises mixing elements can be envisaged.

DRAWINGS

Figure 8:
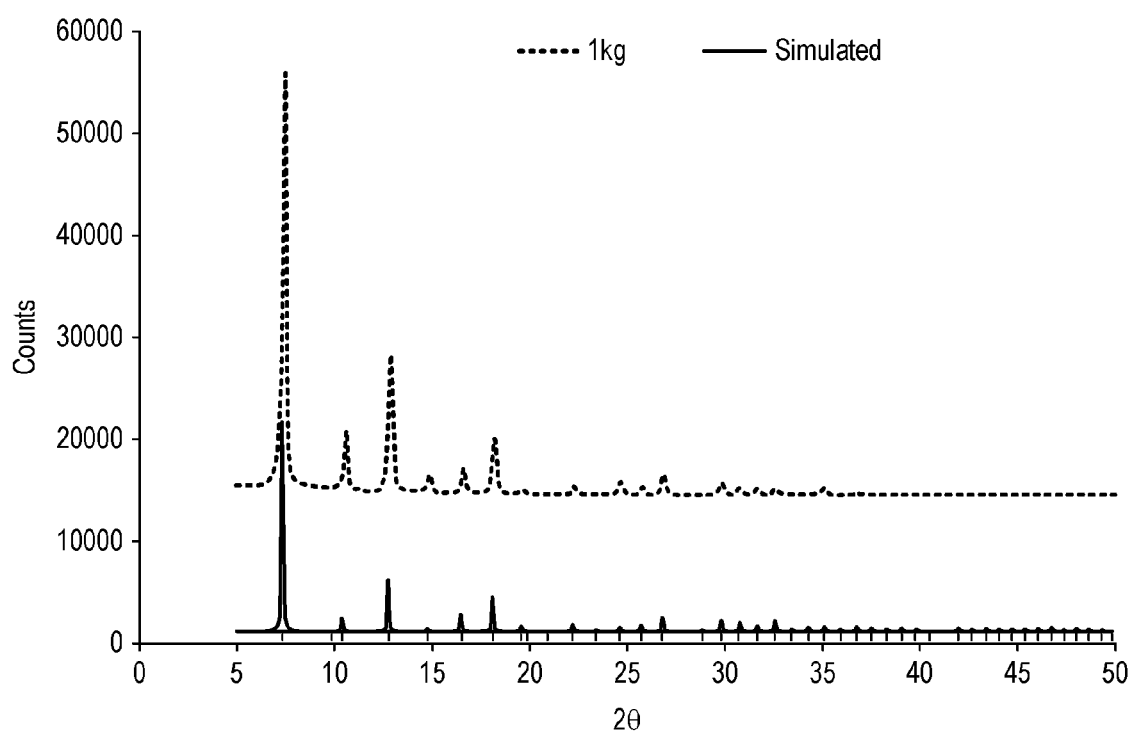
Figure 9:
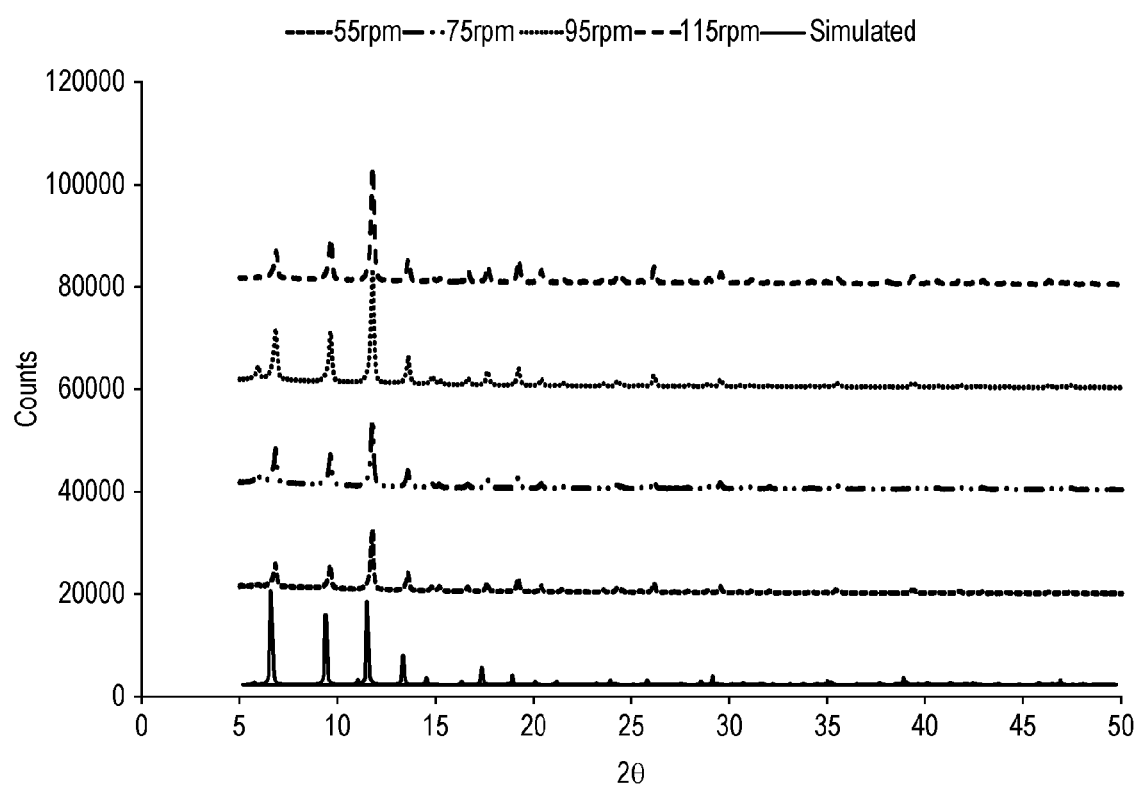
Figure 10:
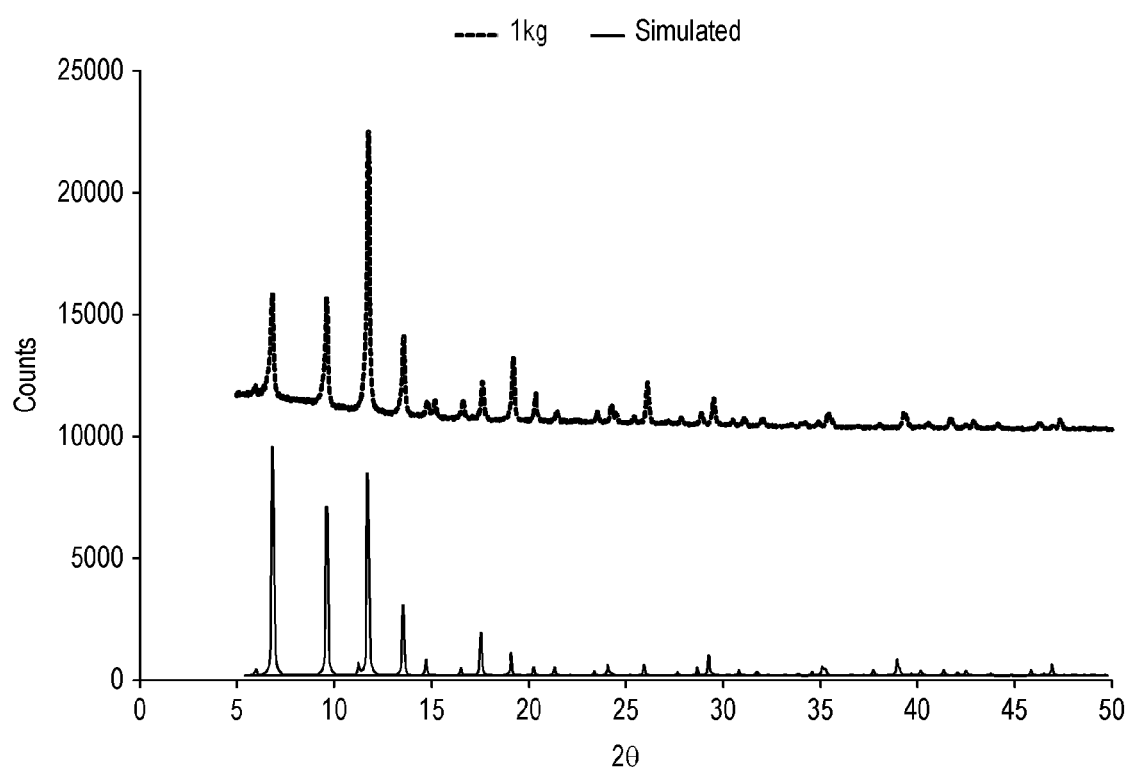
Figure 11:
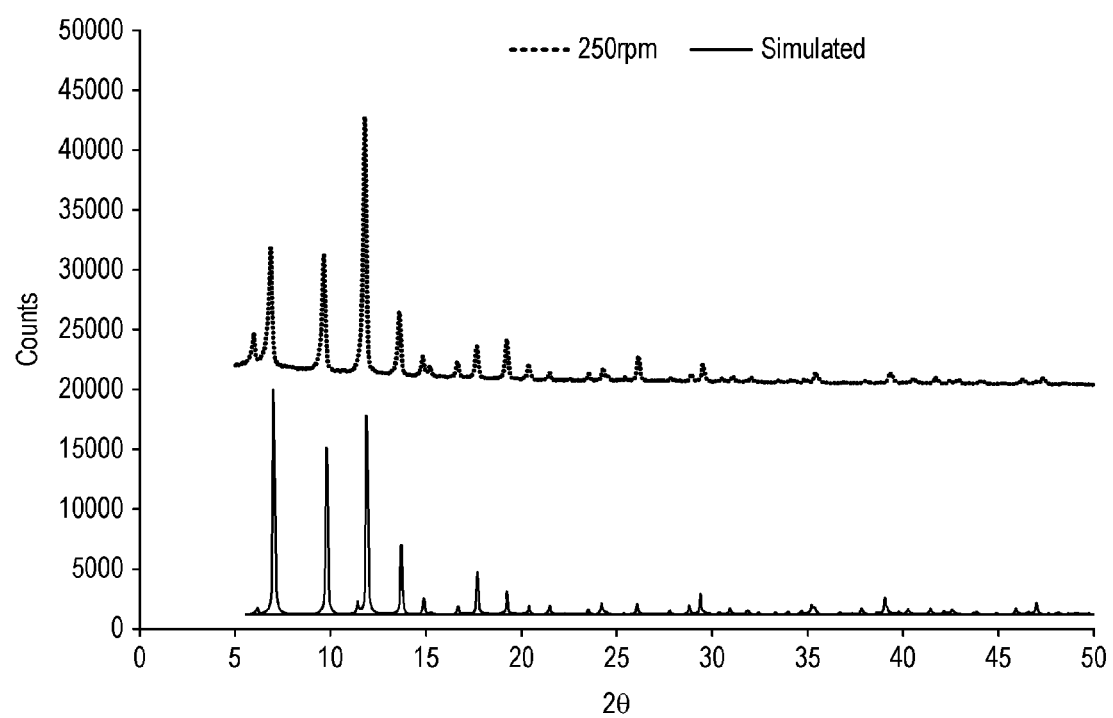
Figure 12:
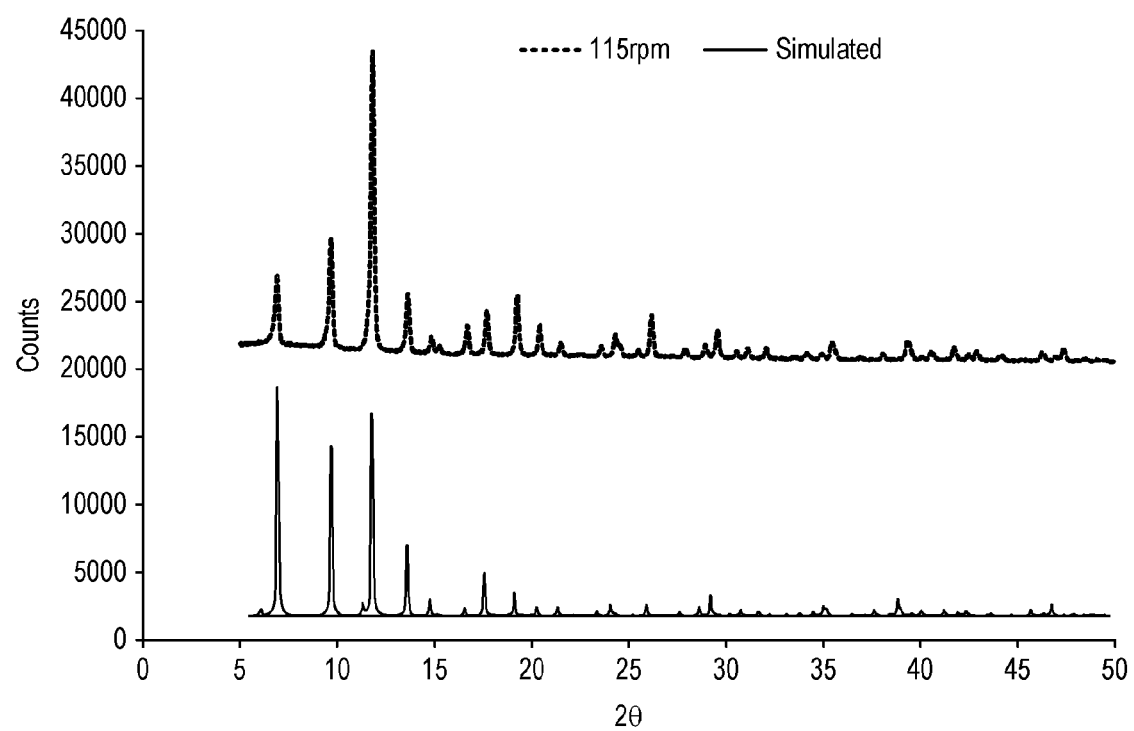
Figure 13:
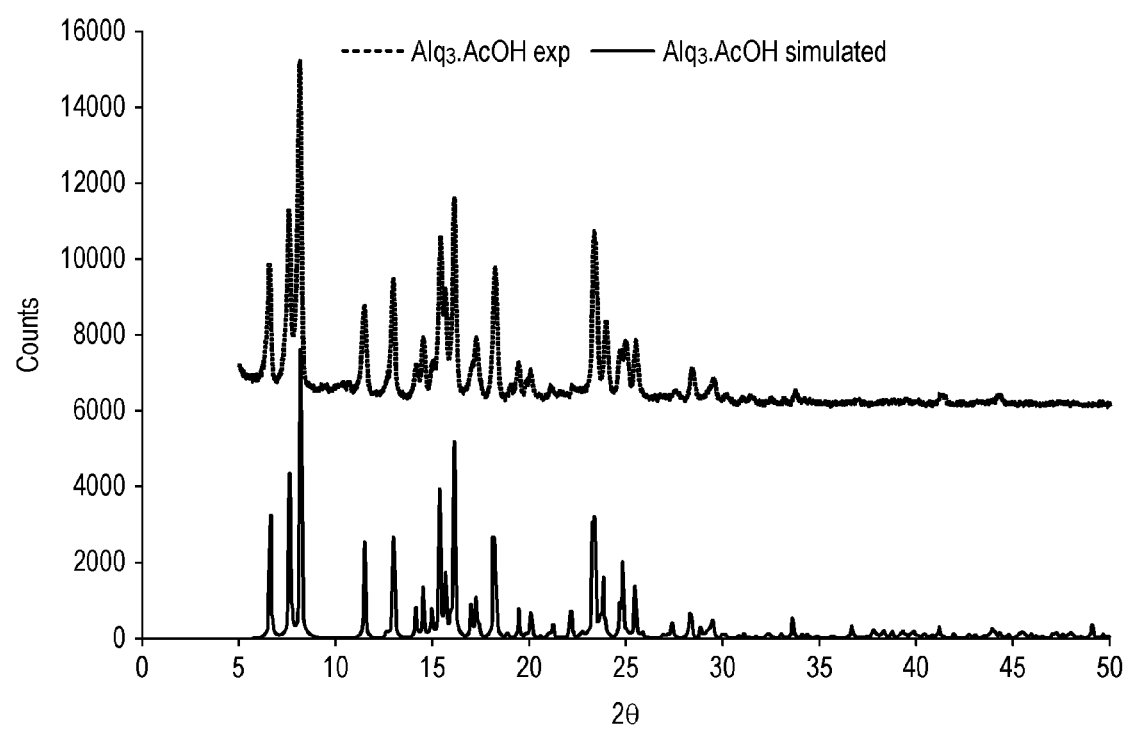
Figure 14:
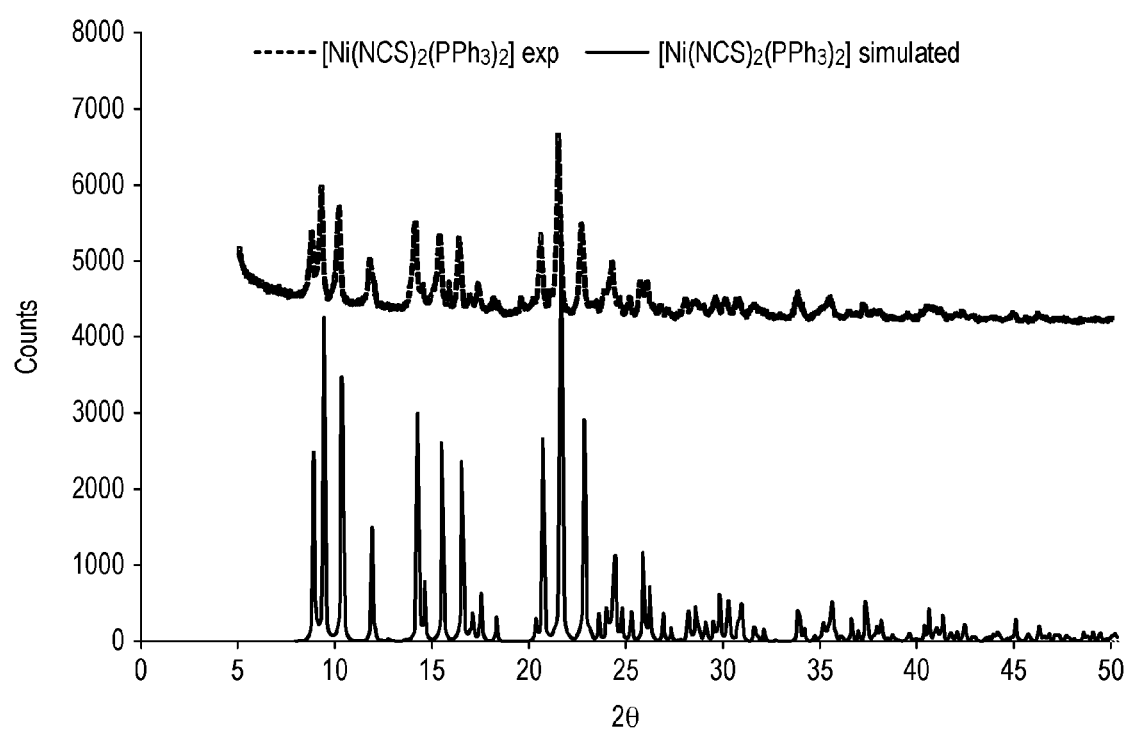

FIG. 8—shows PXRD traces of the activated extrudate from extrusion of 1 kilo of reagents at 95 rpm (- - -) and the simulated PXRD trace of ZIF-8 from CCDC (-);

FIG. 9 shows PXRD traces of the activated extrudate from $Cu_3(BTC)_2$ synthesis at varying speeds;

FIG. 10 shows PXRD traces of the activated extrudate from $Cu_3(BTC)_2$ on a kilo scale;

FIG. 11 shows PXRD traces of the activated extrudate from $Cu_3(BTC)_2$ synthesis with reduced residence time;

FIG. 12 shows PXRD traces of the activated extrudate from $Cu_3(BTC)_2$ synthesis with reduced residence time;

FIG. 13 shows PXRD traces of synthesized $ALq_3$.AcOH (- - -) and the corresponding simulated pattern of $ALq_3$ (-);

FIG. 14 shows PXRD traces of synthesized $[Ni(NCS)_2(PPh_3)_2]$ (- - -) and the corresponding simulated pattern (-)

Figure 15:
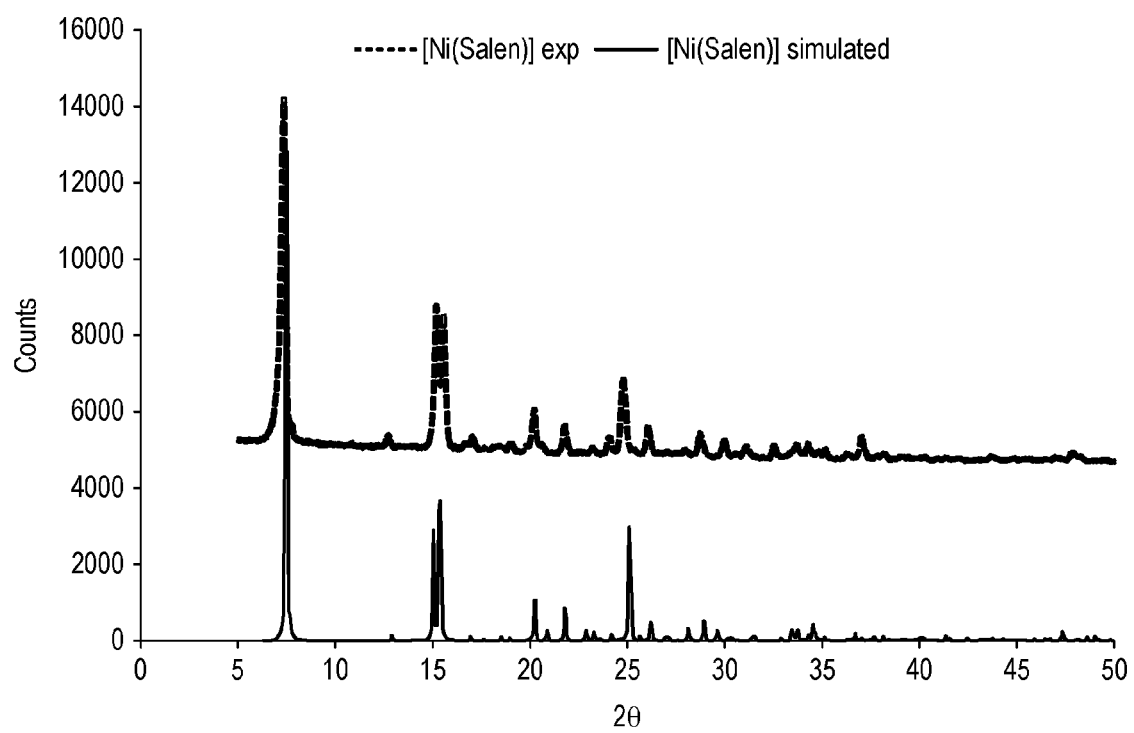
Figure 16:
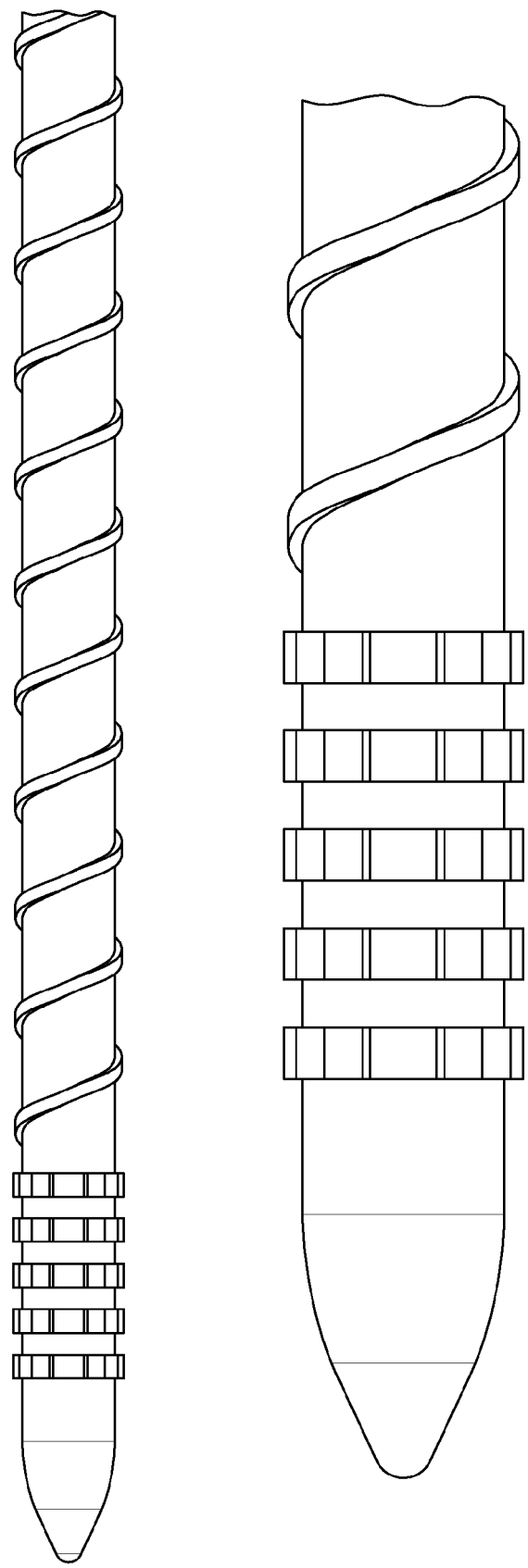
Figure 17:
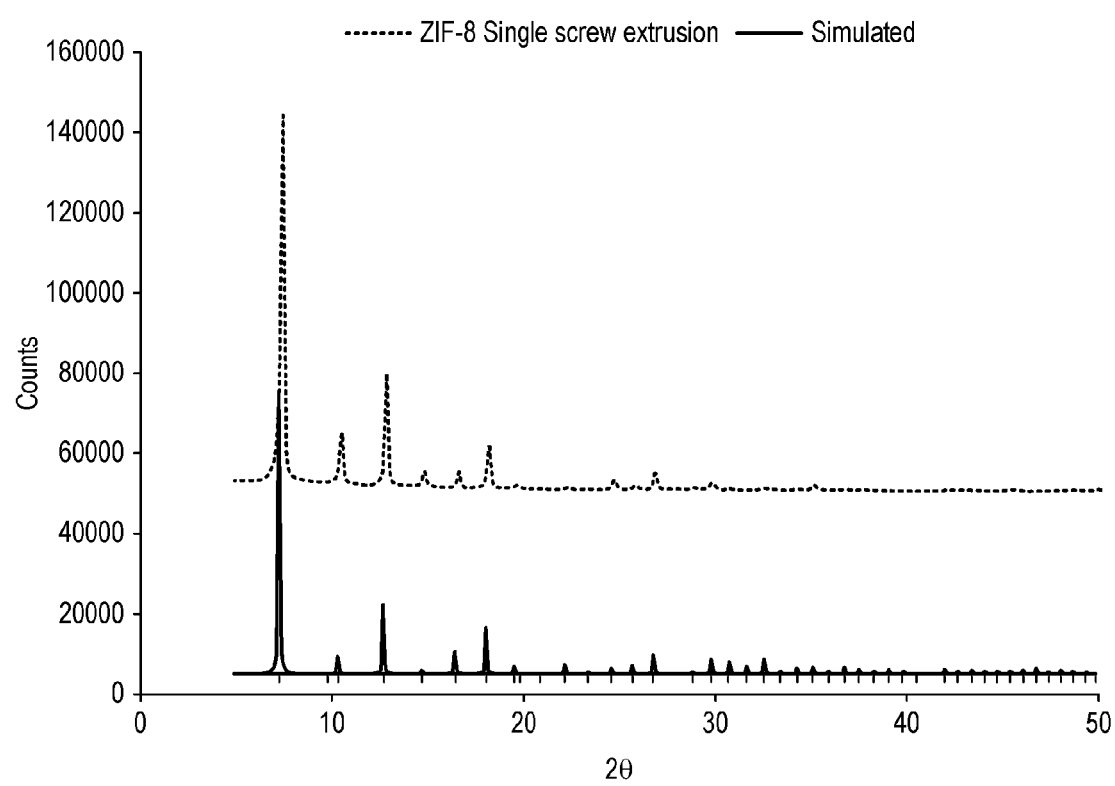

FIG. 15 shows PXRD traces of synthesized [Ni(Salen)] (- - -) and the corresponding simulated pattern (-);

FIG. 16 shows photographs of the PTFE screw used in example 24;

FIG. 17 shows PXRD traces of ZIF-8 prepared from single screw extrusion (- - -) versus the simulated pattern (-) of ZIF-8 taken from CCDC.

EXPERIMENTAL METHODOLOGY

General Aspects

General aspects: Two different models of extruder were used, the Haake Rheomex OS PTW16 co-rotating twin screw extruder and the ThermoFisher Process 11 co-rotating twin screw extruder.

Figure 1:
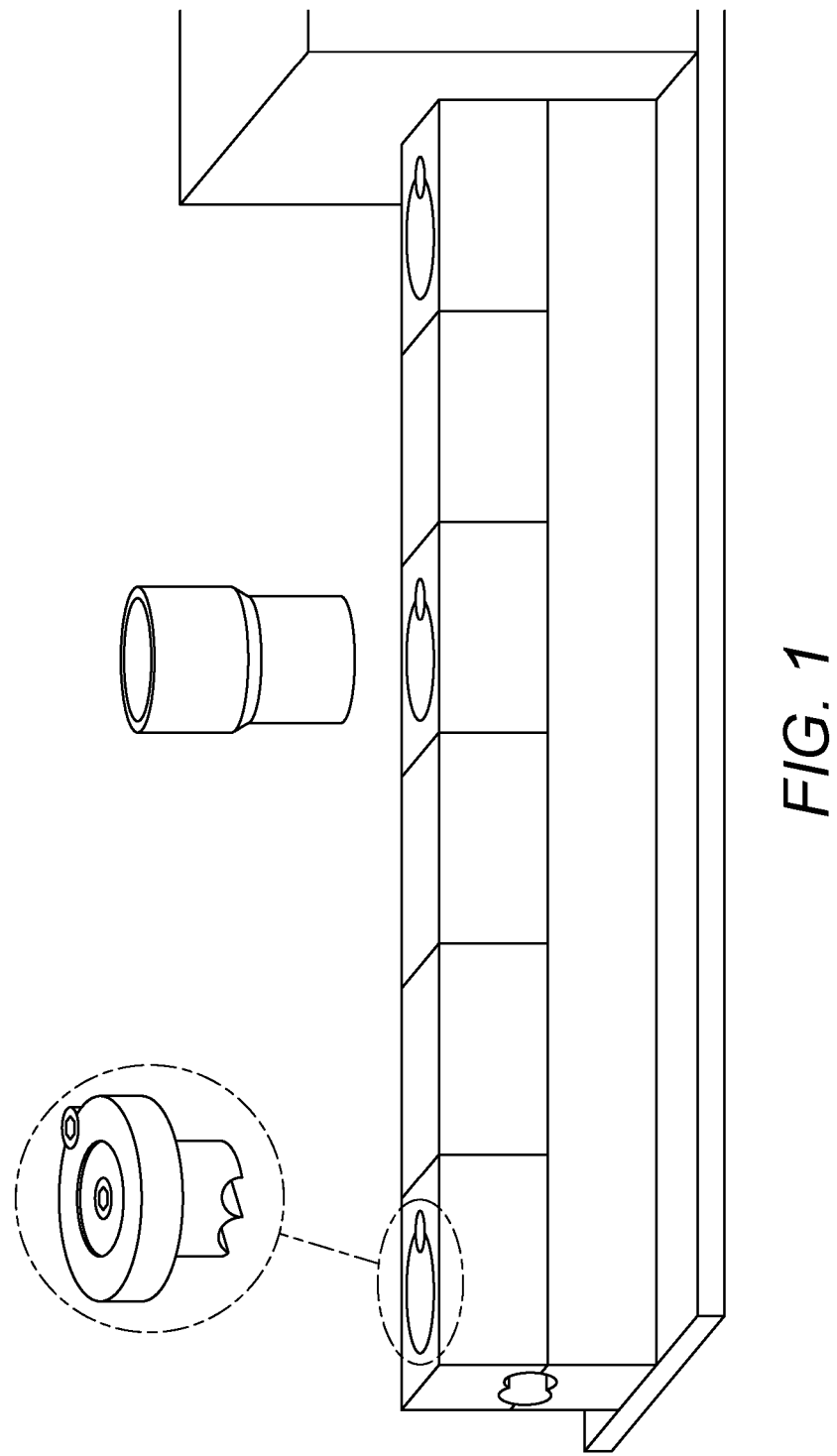
FIG. 1 is a schematic diagram showing the basic layout of the Haake Rheomex and ThermoFisher Process twin screw extruders.

FIG. 1 is a schematic diagram showing the basic layout of both extruders. The lower part of the barrel consists of a single piece, whereas the upper part is assembled in six sections. Some sections contain a plug that can be removed, so that a feeding neck can be inserted. The plug is circled and shows the two Allen-key screws that allow it to be fixed into the barrel and removed. The screws are not shown in this diagram so that the cross sectional shape of the empty barrel can be visualised.

Haake Rheomex

Figure 2:
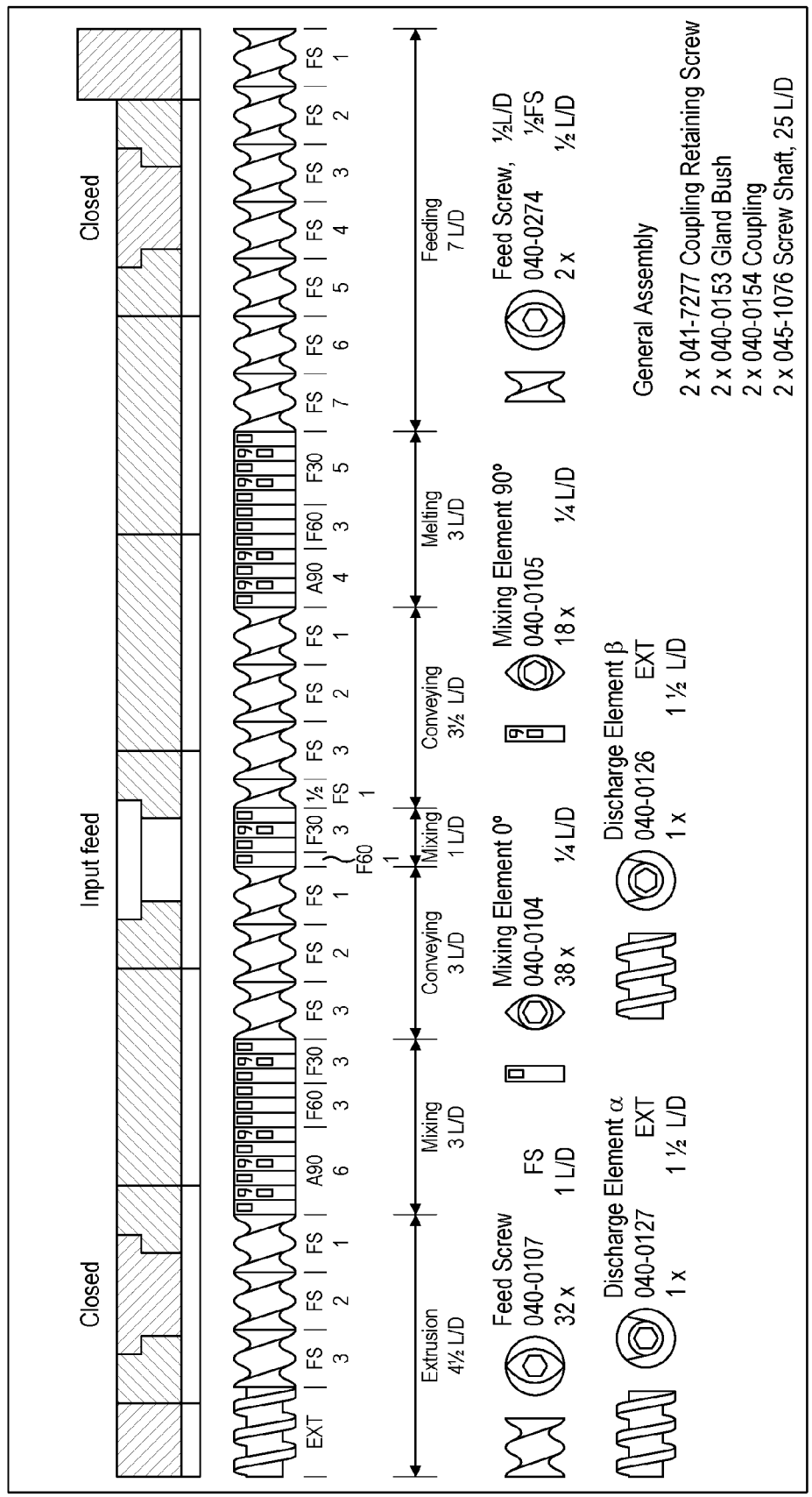
FIG. 2 shows the screw configuration for the Haake Rheomex extruder.

For the Haake Rheomex extruder, a metered feeding system was used. It consists of a simple funnel hopper that drops the material onto a single screw, which then conveys it to an opening allowing it to drop into the extruder barrel. This device has a screw diameter of 16 mm and a screw length to diameter (L/D) ratio of 25:1. It features five temperature-controlled barrel zones and a segmented screw configuration to allow fine control of the extrusion process. The screw configuration used throughout all the experiments on this instrument was FS (×7), F30 (×5), F60 (×3), A90 (×4), FS (×3), FS (½), F30 (×3), F60 (×1), FS (×3), F30 (×3), F60 (×3), F30 (×6), FS (×3), EXT. Specifications for each screw element are contained in the user manual for this equipment. The screw configuration for the Haake Rheomex extruder can be seen in FIG. 2.

ThermoFisher Process 11 Extruder

Figure 3:
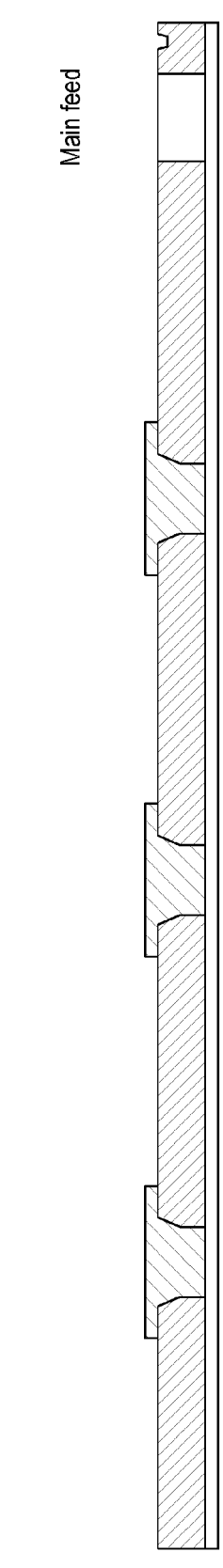
FIG. 3 shows the screw configuration for the ThermoFisher Process 11 extruder.

The ThermoFisher Process 11 extruder used a gravimetric micro twin-screw feeder. The hopper of this was an enclosed cylinder and had three rotating arms upon an axle spaced at 120° to each other. This allowed the continual agitation of the powder before feeding which prevents particles from adhering together. The screw configuration used throughout all the experiments on this instrument was FS (×9), F30 (×5), F60 (×3), A90 (×4), FS (×7), F60 (×6), FS (×8), F60 (×4), A90 (×8), FS (×7), EXT. Specifications for each screw element are contained in the user manual for this equipment. The, screw configuration for the ThermoFisher Process 11 can be seen in FIG. 3.

A cleaned extruder was pre-heated to the selected processing temperature. A range of barrel temperature profiles were used, typically increasing from a cooled feed zone to a maximum mid-way along the barrel and decreasing towards the die end. For the purposes of these experiments the extruders were run without a die. Extruder screw rotation speed was set; a wide range of speeds can be achieved, up to 1000 revolutions per minute (rpm) with the extruder used here. Typical screw rotation speeds were set at between 40 and 70 rpm. A pre-mixed blend of metal salt and organic ligand reactants were then introduced into the feed hopper of the extruder. Manual dosing may prove convenient for small batch sizes (typically between 10-200 g). For larger batch sizes a gravimetric or volumetric feeder system can more conveniently be employed. The extruded product was then collected at the exit of the screws, in powder, sticky mass or molten form depending upon constituents and the set operating conditions. The collected material was subsequently analysed for metal organic compound formation.

During the course of experiments, the following parameters could be adjusted:

Set temperature
Screw rotation speed
Throughput
Screw design (i.e. degree of distributive and dispersive mixing)
Number of passes through the extruder
Ratio of precursors
Type of added solvent
Amount of added solvent Inspection of the process by removal of the top of the barrel in order to view the reacting materials showed no evidence of the formation of a liquid phase.

Example 1—Zn MOF (ZIF-8)

A physical mixture of basic zinc carbonate and 2-methylimidazole was prepared by mixing 40 g $[ZnCO_3]_2[Zn(OH)_2]_3$ and 60 g $C_4H_6N_2$ (HMIM) (molar ratio 10:1) in a cup. The Haake Rheomex extruder was used with the screw configuration detailed above, consisting primarily of forward feeding elements and a small distributive mixing zone. The barrel of the extruder was at room temperature. The physical mixture was slowly fed to the extruder at a rate of 5 g/minute and the screws were rotated at 55 rpm. The finely agglomerated product was collected at the extruder exit and then recirculated through the extruder four further times. On the fourth pass through the extruder, 8 mL of MeOH was also fed into the extruder.

The resulting powder (Material 1) was collected. A 1 g sample of Material 1 was subjected to powder X-ray diffractometric (PXRD) characterisation. The X-ray diffraction pattern of the Material 1 was sufficiently similar to that calculated for the previously known metal-organic framework ZIF-8 to suggest that a reaction between the precursors had taken place to produce the metal organic framework ZIF-8. The comparative PXRD data were simulated from the single crystal X-ray diffraction data in the Cambridge Structural Database.

A 2.5 g sample of Material 1 was washed and activated by immersing in 100 mL of MeOH for 20 minutes and then placed in an oven at 150° C. for 2 hours. The sample was then subjected to BET surface area analysis, giving a very high surface area of 1417 $m^2/g$.

Figure 4:
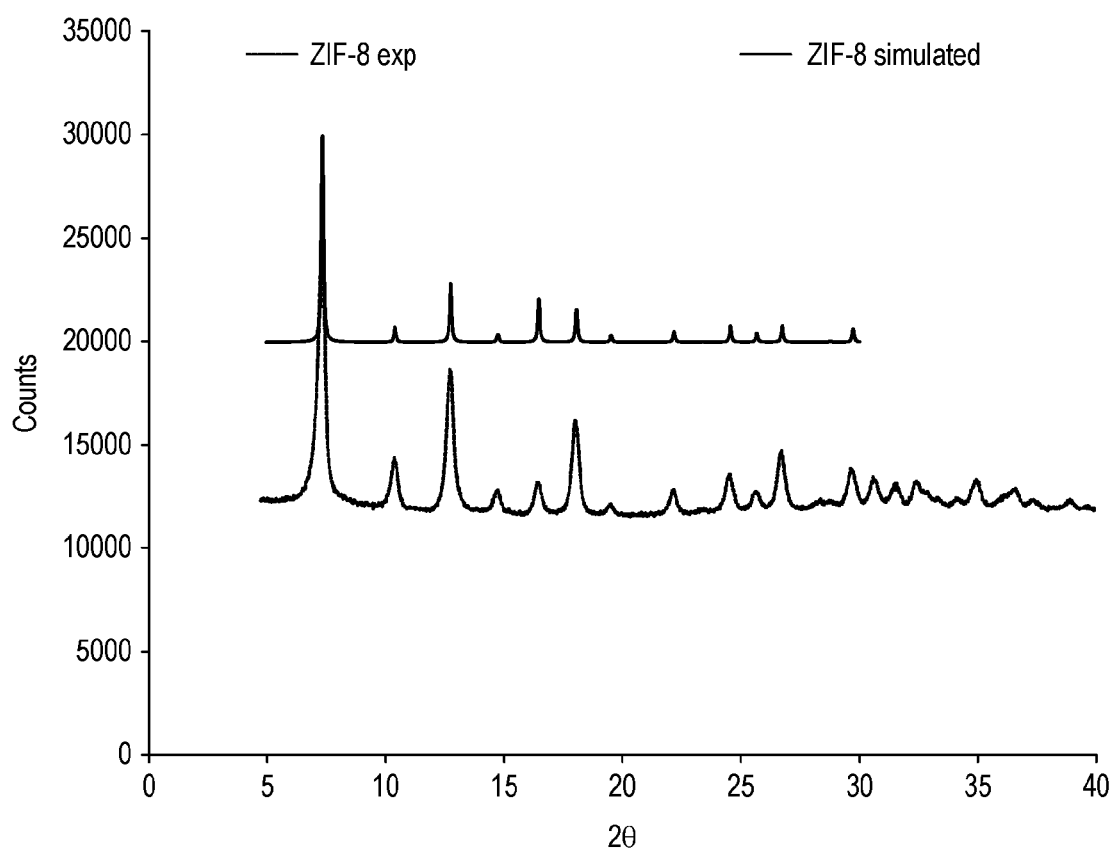
FIG. 4 shows simulated and experimental PXRD patterns relating to the synthesis of ZIF-8 by extrusion.

FIG. 4 shows the PXRD patterns (simulated and experimental) obtained for material 1, alongside the theoretical PXRD pattern for known metal organic framework ZIF-8.

Based on the above method, related materials can be prepared based on other metals such as ZIF-67 (by reaction of cobalt hydroxide with 2-methylimidazole), or based on other organic molecules such as ZIF-7 (by reaction between basic zinc carbonate and benzimidazole), $Cu(isonicotinate)_2$ (by reaction between isonicotinic acid and $Cu(OAc).H_2O$), Mg(isonicotinate)2 (by reaction between Mg(OH)2 and isonicotinic acid), Li(isonicotinate) (by reaction between LiOH and isonicotinic acid) and Mn(isonicotinate)2 (by reaction between $Mn(OAc)_2$ and isonicotinic acid).

Example 2—Cu MOF (CuBTC)

A physical mixture of copper acetate monohydrate and 1,3,5-benzenetricarboxylic acid was prepared by mixing 58.8 g $Cu(OAc)_2.H_2O$ and 41.4 g of $H_3BTC$ (molar ratio 3:2) in a cup. The Haake Rheomex extruder was used with the screw configuration detailed above, consisting primarily of forward feeding elements and a small distributive mixing zone. The barrel of the extruder was at room temperature. The physical mixture was slowly fed to the extruder at a rate of 5 g/minute and the screws were rotated at 55 rpm. The finely agglomerated product was collected at the extruder exit and then recirculated through the extruder two further times. On the second pass through the extruder, 20 mL of MeOH was also fed into the extruder.

The resulting powder (Material 2) was collected. A 1 g sample of Material 2 was subjected to powder X-ray diffractometric (PXRD) characterisation. The X-ray diffraction pattern of the Material 2 was sufficiently similar to that calculated for the previously known metal-organic framework CuBTC (HKUST-1) to suggest that a reaction between the precursors had taken place to produce the metal organic framework CuBTC (HKUST-1). The comparative PXRD data were simulated from the single crystal X-ray diffraction data in the Cambridge Structural Database.

A 2.5 g sample of Material 2 was washed and activated by immersing in 100 mL of EtOH for 20 minutes and then placed in an oven at 150° C. for 2 hours. The sample was then subjected to BET surface area analysis, giving a surface area of 706 m$^2$/g.

Figure 5:
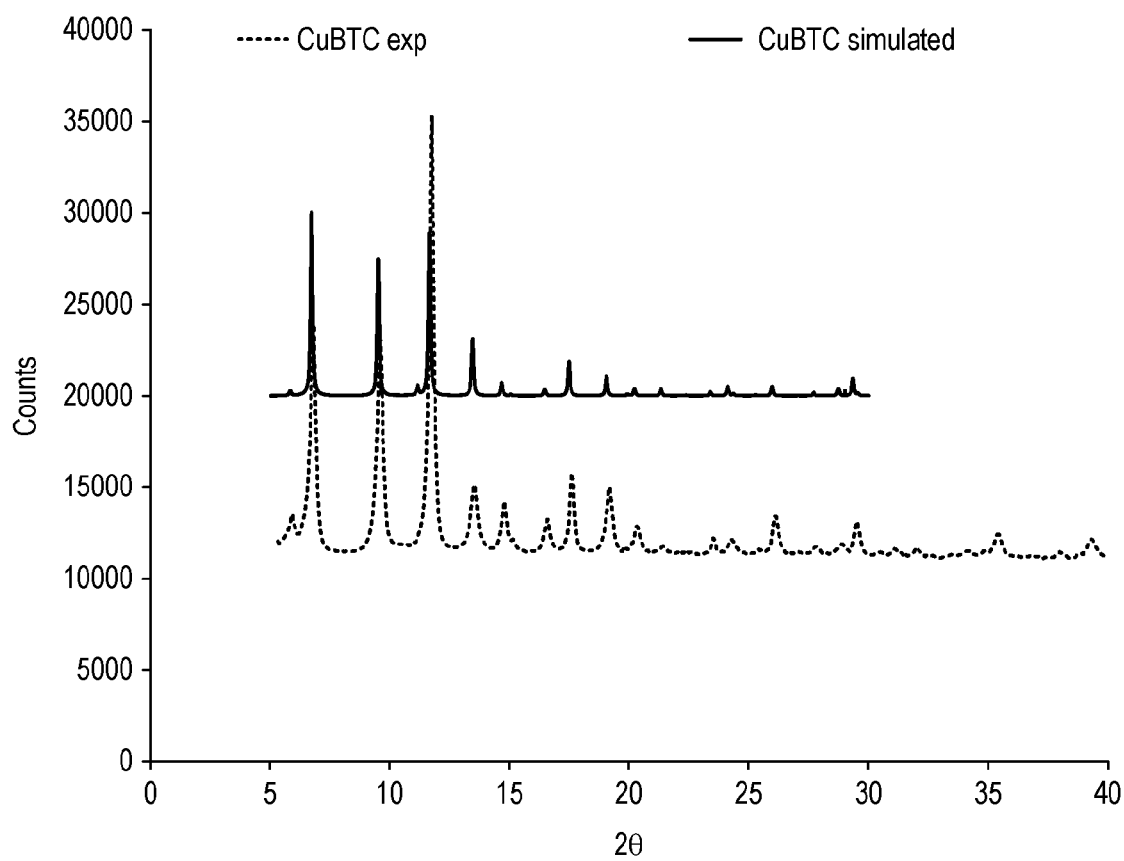
FIG. 5 shows simulated and experimental PXRD patterns relating to the synthesis of CuBTC by extrusion.

FIG. 5 shows the PXRD patterns (simulated and experimental) obtained for Material 2, alongside the theoretical PXRD pattern for known metal organic framework CuBTC (HKUST-1).

Based on the above example, related materials can be prepared based on alternative metals such as Fe(BTC) (by reacting Fe(OAc)$_3$ with H$_3$BTC) or La(BTC) (by reaction between La$_2$(CO$_3$)$_3$ and H$_3$BTC) on alternative organic linkers such as MOF-74(Zn) (by reaction between basic zinc carbonate and 2,5-dihydroxyterephthalic acid), MOF-74 (Mg) (by reaction between Mg(OH)$_2$ and 2,5-dihydroxyterephthalic acid), MOF-74(Co) (by reaction between Co(OH)2 and 2,5-dihydroxyterephthalic acid), MOF-74(Fe) (by reaction between Fe(OAc)$_2$ and 2,5-dihydroxyterephthalic acid), MIL-53 (by reaction between Al(OH) (OAc)$_2$ and terephthalic acid).

Example 3—Zn Complexes of 8-Hydroxyquinoline

Zn-quinolinate complexes were synthesized as detailed below. Complexes were synthesized from zinc acetate dehydrate and from basis zinc carbonate. The HAAKE Rheomex PTW16 OS extruder and the ThermoFisher Process 11 extruder were used as indicated in the experimental sections below.

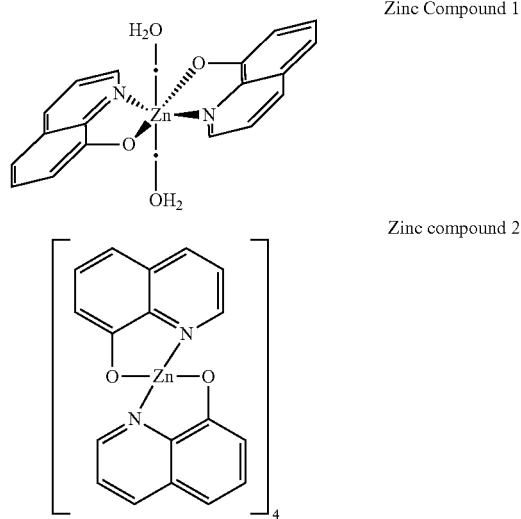

Structures of Zn-quinolinate complexes obtained by extrusion and referred to in example 3.

Example 3(i)—Synthesis from Zinc Acetate Dihydrate

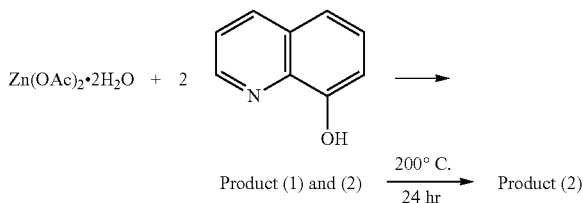

Method A (Haake Rheomex 16):

Both reactants were pre-ground in a vibrational ball mill and sieved through industrial standard sieves (355 μm mesh). Zinc acetate dihydrate (43 g, 1.95 mol) was hand mixed with 8-hydroxyquinoline (57 g, 0.393 mol) for 5 minutes. The mixture was put in a hopper fed to the extruder barrel with a metering based feed screw at an approximate rate of 3 g/minute. The material was hand fed at an approximate rate of 3 g/min. The material was extruded at 55 rpm without applied heat to the barrel and a yellow/lime green material was collected. Analysis by PXRD showed the product to consist of a mixture of products (1) and (2).

Method B (ThermoFisher Process 11):

8-hydroxyquinoline was pre-ground by hand in a large pestle and mortar, so that the diameter of the particles matched those of the zinc salt (between 1-3 mm). Zinc acetate dihydrate (43 g, 1.95 mol) was hand mixed with 8-hydroxyquinoline (57 g, 0.393 mol) for 5 minutes. The mixture was put in a hopper fed to the extruder barrel from at an exact rate of 1.33 g/minute. The hopper had a mechanical mixer in it, and a twin screw gravimetric feeder. The material was extruded at 200 rpm with the barrel temperature set at 50° C. A homogenous green material was collected Analysis by PXRD showed the product to consist of a mixture of products (1) and (2).

Method C (ThermoFisher Process 11):

Both reactants were pre-ground in a vibrational ball mill and sieved through industrial standard sieves (355 μm mesh). Zinc acetate dihydrate (43 g, 1.95 mol) was hand mixed with 8-hydroxyquinoline (57 g, 0.393 mol) for 5 minutes. The mixture was put in a hopper and fed to the extruder barrel from at an exact rate of 1.33 g/minute. The hopper contained mechanical mixer, which prevented aggregation of the mixture and kept it as a free-flowing powder. A twin screw gravimetric feeder designed for powder feeding was used. The material was extruded at 200 rpm with of the barrel temperature set at 50° C. A homogenous green material was collected. Analysis by PXRD showed the product to consist of a mixture of products (1) and (2).

Example 3(ii)—Synthesis from Basic Zinc Carbonate

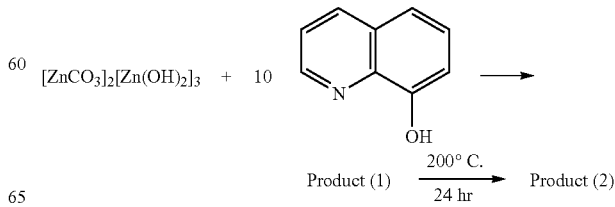

Method A (Haake Rheomex 16):

8-hydroxyquinoline was pre-ground in a vibrational ball mill and both reactants sieved (355 μm mesh). Basic zinc carbonate (20.55 g, 0.0374 mol) was added to 8-hydroxyquinoline (54.44 g, 0.375 mol) and hand mixed for 5 minutes. The mixture was put in a hopper fed to the extruder barrel with a metering based feed at an approximate rate of 3 g/minute. The material was extruded at 200 rpm with the barrel temperature set at 50° C. After collecting an initial 5-10 g of a feint yellow powder, a mustard yellow, flaky material was collected. Analysis by PXRD showed it to consist of product (1).

Method C (ThermoFisher Process 11):

The 8-hydroxyquinoline reactant was pre-ground in a vibrational ball mill and both reactants sieved (355 μm mesh). Basic zinc carbonate (20.55 g, 0.0374 mol) was added to 8-hydroxyquinoline (54.44 g, 0.375 mol) and hand mixed for 5 minutes. The mixture was placed in a hopper and fed to the extruder barrel at an exact rate of 1.33 g/minute. The hopper contained mechanical mixer, which prevented aggregation of the mixture and kept it as a free-flowing powder. A twin screw gravimetric feeder designed for powder feeding was used. The material was extruded at 200 rpm with the barrel temperature set to 50° C. After collecting about 5-10 g of the faint yellow powder, a mustard yellow, flaky material was collected. Analysis by PXRD showed it to consist of product (1).

Based on the above example related complexes can be prepared such as Al(8-quinolinate)$_3$ (by reaction between Al(OH)(OAc)$_2$ and 8-hydroxyquinoline or Mg((8-quinolinate)$_2$ (by reaction between Mg(OH)2 and 8-hydroxyquinoline).

Examples 4 to 10

The HAAKE RHEOMEX PTW16 OS extruder was used in Examples 4 to 10 below. The screw speed was set at 55 rpm. The effect of the temperature on the synthesis of MOFs was evaluated by increasing the temperature of the five heated zones of the barrel from room temperature (25° C.) to 150° C. The reagents were pre-mixed and manually fed afterwards, using the first feed port at an addition rate of approximately 5 g/minute. The effect of liquid-assisted grinding was evaluated by manual addition of absolute MeOH to the solid mixture. The MOFs were activated with absolute EtOH, MeOH or H$_2$O, as detailed below. The solid products were recovered by vacuum filtration and dried at 150° C. for 2 h in a Carbolite PF60 furnace (serial number 20-601895).

Example 4(i)—Cu$_3$(BTC)$_2$ 41.05 g of Cu(OH)$_2$ (0.42 mol) and 58.95 g of 1,3,5-benzenetricarboxylic acid (0.28 mol) were pre-mixed in a cup. 30 mL of MeOH were added to the mixture and the resulting solid was passed through the extruder at room temperature. Finally, 30 mL more of MeOH were added to the mixture and the solid was extruded at room temperature a second time. The XRD patterns of the extruded materials confirmed the formation of CuBTC, even for the material that had only been extruded with 30 mL of MeOH. Activation of CuBTC was carried out by washing 1 g of the blue MOF with 40 mL of absolute ethanol for 20 min (×3). BET analysis confirmed the high surface area of the activated product (1324 m$^2$/g).

TABLE 1

|  | metal | linker(s) | MOF |
| --- | --- | --- | --- |
| 1 | Zn | 2-methyl imidazole | Zn(Me-im)$_2$ ZIF-8 |
| 2 | Zn | 2-ethylimidazole |  |
| 3 | Zn | benzimidazole | ZIF-7 |
| 4 | Zn | trans-1,4-butene dicarboxylic acid (fumaric acid) and dabco/4,4'-bipyridine | Zn$_2$(fumarate)$_2$(dabco) or Zn$_2$(fumarate)$_2$(bipyridine) or |
| 5 | Co | 2-methyl imidazole | Co(Me-im)$_2$ ZIF-67 |
| 6 | Mg | Isonicotinic acid | Mg(INA)$_2$ |
| 7 | Cu | Isonicotinic acid | Cu(INA)$_2$ |
| 8 | Al | 1,4-benzenedicarboxylic acid (terephthalic acid) | Al(bdc)OH MIL-53 |
| 9 | Lanthanide | 1,3,5-benzenetricarboxylic acid | Ln(btc) |
| 10 | Cu | 1,3,5-benzenetricarboxylic acid | Cu$_3$(btc)$_2$ HKUST-1 |
| 11 | Fe | 1,3,5-benzenetricarboxylic acid | Fe(BTC) |
| 12 | Li | Isonicotinic acid | Li(INA) |
| 13 | Sc | 1,4-benzenedicarboxylic acid (terephthalic acid) | Sc(terephthalate) |
| 14 | Mn | Isonicotinic acid | Mn(INA)$_2$ |
| 15 | Cr | 1,4-benzenedicarboxylic acid (terephthalic acid) | MIL-101 |
| 16 | Ti | 1,4-benzenedicarboxylic acid (terephthalic acid) | MIL-125 |
| 17 | Zn | 2,5-dihydroxybenzene1,4-dicarboxylic acid | MOF-74 (Zn) |
| 18 | Mg | 2,5-dihydroxybenzene1,4-dicarboxylic acid | MOF-74 (Mg) |
| 19 | Co | 2,5-dihydroxybenzene1,4-dicarboxylic acid | MOF-74 (Co) |
| 20 | Fe | 2,5-dihydroxybenzene1,4-dicarboxylic acid | MOF-74 (Fe) |

Example 4(ii)—Alternative Synthesis of CuBTC Using Copper Acetate 58.8 g of Cu(OAc)$_2$.H$_2$O (0.30 mol) and 41.2 g of 1,3,5-benzenetricarboxylic acid (0.20 mol) were pre-mixed in a cup. The solvent-free mixture was passed through the extruder at room temperature while 20 mL of MeOH were added at a rate of 1 mL/min using a second feed port. Finally, the mixture was passed through the extruder one last time without adding any more MeOH. XRD analysis of the extruded materials confirmed the formation of the CuBTC MOF. BET analysis of the activated product with absolute ethanol confirmed the high surface area of the MOF (706 m$^2$/g).

Example 5(i)—Synthesis of ZIF-8

30.76 g of [ZnCO$_3$]$_2$[Zn(OH)$_2$]$_3$ (0.056 mol) and 69.24 g of 2-methylimidazole (0.84 mol) were pre-mixed in a cup. The solid mixture was then passed through the extruder at 150° C. The solid sample was then passed through the extruder a second time at 150° C. The XRD patterns of the extruded materials confirmed the formation of ZIF-8, even for the material that had only been extruded once. Activation of the samples was carried out by washing 2.5 g of ZIF-8 with 50 mL of methanol for 20 min (×3) in order to remove the unreacted excess of 2-methylimizadole.

Example 5(ii)—Synthesis of ZIF-8

Alternative synthesis of ZIF-8 at room temperature was also investigated. Liquid-assisted grinding (LAG) with methanol was carried out. The same solid mixture was passed through the extruder while 7 mL of MeOH were added using a second port. Finally, the solid mixture was passed through the extruder at room temperature a third time. The XRD analysis confirmed the formation of the MOF and BET analysis of the activated product confirmed the high surface area of ZIF-8 (1614 m$^2$/g).

Excess of 2-methylimidazole was used in the synthesis of ZIF-8 because previous work had showed that lower surface areas were obtained when stoichiometric quantities were used. Synthesis of ZIF-8 by extrusion at 150° C. using stoichiometric quantities (40 g of [ZnCO$_3$]$_2$[Zn(OH)$_2$]$_3$ (0.073 mol) and 60 g of 2-methylimidazole (0.730 mol), resulted in ZIF-8 with a surface area of 1253 m$^2$/g.

Example 6—Synthesis of ZIF-67

36.15 g of Co(OH)$_2$, m.p. 168° C. (0.39 mol) and 63.85 g of 2-methylimidazole, m.p. 144° C. (0.78 mol) were pre-mixed in a cup and the solvent-free mixture was passed through the extruder at 150° C. The solid product was then extruded again a second time at 150° C. The XRD patterns of the extruded materials (even for the product extruded once) exhibited the characteristic diffraction peaks of ZIF-67, confirming the formation of the MOF.

ZIF-67 was activated by washing 2.5 g of the purple MOF with 50 mL of MeOH for 20 min (×3). The XRD pattern of the activated product did not show any significant differences compared to the material obtained directly from the extruder. The BET analysis of the activated product confirmed its high surface area (1232 m$^2$/g).

It should be noted that the characteristic diffraction peaks of ZIF-67 were not present on the XRD pattern of the extruded product when the same solid mixture was extruded at room temperature. However, upon activation with MeOH, the diffraction peaks corresponding to the MOF were detected, confirming the formation of ZIF-67.

Example 7—Synthesis of Mg-MOF-74

37.06 g of Mg(OH)$_2$ (0.64 mol) and 62.94 g of 2,5-dihydroxibenzene-1,4-dicarboxylic acid (0.32 mol) were pre-mixed in a cup. 10 mL of MeOH were added to the solid mixture while it was stirred with a spatula and the resulting solid was passed through the extruder at room temperature. 10 more mL of MeOH were then added to the extruded solid while stirring with a spatula and the resulting solid mixture was passed through the extruder at room temperature a second time. Finally, 10 more mL of MeOH were added to the solid mixture and the resulting solid powder was passed through the extruder at room temperature a third time. PXRD analysis of the product confirmed the formation of Mg-MOF-74. Mg-MOF-74 was activated by washing 1 g of the yellow MOF with 60 mL of degassed MeOH for 18 h and filtered under N$_2$. The BET analysis of the activated product confirmed its high surface area (684 m$^2$/g).

Example 8—Synthesis of Co-MOF-74

48.41 g of Co(OH)$_2$ (0.52 mol) and 51.59 g of 2,5-dihydroxibenzene-1,4-dicarboxylic acid (0.26 mol) were pre-mixed in a cup. 10 mL of MeOH were added to the cup containing the solid mixture while it was stirred with a spatula and then the solid mixture was passed through the extruder at room temperature. 10 more mL of MeOH were then added to the mixture while stirring with a spatula and the resulting solid was passed through the extruder at room temperature a second time. Finally, 10 more mL of MeOH were added to the solid mixture and the resulting solid was passed through the extruder at room temperature a third time. XRD analysis of the product confirmed the formation of Co-MOF-74. Activation of the MOF was carried out by washing 2.5 g of Co-MOF74 with 50 mL of MeOH for 20 min (×3). However, the XRD pattern of the activated MOF did not show any significant differences compared to the material obtained directly from the extruder.

Example 9—Synthesis of Zn-MOF-74

52.48 g of [ZnCO$_3$]$_2$[Zn(OH)$_2$]$_3$ (0.096 mol) and 47.52 g of 2,5-dihydroxibenzene-1,4-dicarboxylic acid (0.240 mol) were pre-mixed in a cup. 10 mL of MeOH were added to the cup containing the solid mixture while it was stirred with a spatula and the resulting solid was passed through the extruder at room temperature. 10 more mL of MeOH were then added to the solid while stirring with a spatula and the solid mixture was passed through the extruder at room temperature a second time. Finally, 10 more mL of MeOH were added to the solid while stirring with a spatula and the resulting solid was passed through the extruder at room temperature a third time. XRD analysis of the product confirmed the formation of Zn-MOF-74. Activation of the MOF was carried out by washing 2.5 g MOF with 50 mL of MeOH for 20 min (×3). However, the XRD pattern of the activated MOF did not show any significant differences compared to the material obtained directly from the extruder.

Example 10—Synthesis of Al(OH) Fumarate 74.48 g of Al$_2$(SO$_4$)$_3$.18H$_2$O (0.11 mol), 25.94 g of fumaric acid (0.22 mol) and 26.64 g of NaOH pellets (0.66 mol) were pre-mixed in a cup and then the solvent-free mixture was passed through the extruder at room temperature. After that, the solid was passed through the extruder at room temperature a second time without adding any solvent. Finally, the solid was the solid was passed through the extruder at room temperature a third time without adding any solvent. The XRD patterns of the materials passed through the extruder twice and three times showed the characteristic diffraction peaks of Al(OH)fumarate, confirming the formation of the MOF. However, $Na_2SO_4$ (formed as a biproduct) was also detected on the XRD patterns. Activation of the MOF was carried out by washing 1 g of product with 30 mL of $H_2O$ for 20 min (×3). The XRD pattern of the activated product showed only the diffraction peaks corresponding to Al(OH)fumarate, confirming that the $Na_2SO_4$ had been removed. High surface area of the activated Al(OH)fumarate MOF prepared by extrusion was confirmed by BET analysis (1010 $m^2$/g).

It should be noted that when the same mixture of solids was passed through the extruder at 150° C., the characteristic diffraction peaks of the aluminium MOF were detected even for the material extruded once.

In addition, further work showed that the process could be optimised. Higher feed rates (10 g/min) were achieved by increasing the screw speed up to 95 rpm and by using NaOH pearls. BET analysis of the activated material confirmed the high surface area of the MOF produced even when activated in large scale (945 $m^2$/g for the product activated in 14 g scale).

Example 11—Synthesis of ZIF-8 at 150° C.

Basic zinc carbonate, $[ZnCO_3]_2.[Zn(OH)_2]_3$ (30.81 g, 0.056 moles) and 2-methylimidazole (69.18 g, 0.84 moles) were physically mixed together (Molar ratio 1:15). These were manually fed into the Haake Rheomex OS PTW16 at a range of speeds—55, 75 and 95 rpm. The screws consisted mainly of forward conveying sections and two kneading sections. The barrel of the extruder was set at 150° C. A beige molten extrudate was collected from each experiment that solidified quite quickly upon cooling to room temperature. The extrudate was extruded at the same speed a further two times, however the second extrusion was quite difficult to feed due to the shaped 'clumps' formed upon cooling. Throughput rates from the first extrusion were determined and are outlined in Table 2.

TABLE 2

| Screw Speed (rpm) | Throughput Time (mins) | Throughput Rate (kg/hr) |
| --- | --- | --- |
| 55 | 18 | 0.33 |
| 75 | 10 | 0.60 |
| 95 | 6 | 1.00 |

PXRDs of the as-synthesised ZIF-8 extrudates were sufficiently similar to the simulated PXRD pattern of ZIF-8 obtained from the single crystal X-ray diffraction data in the Cambridge Structural Database. PXRD traces indicated a complete reaction following the first extrusion.

Figure 6:
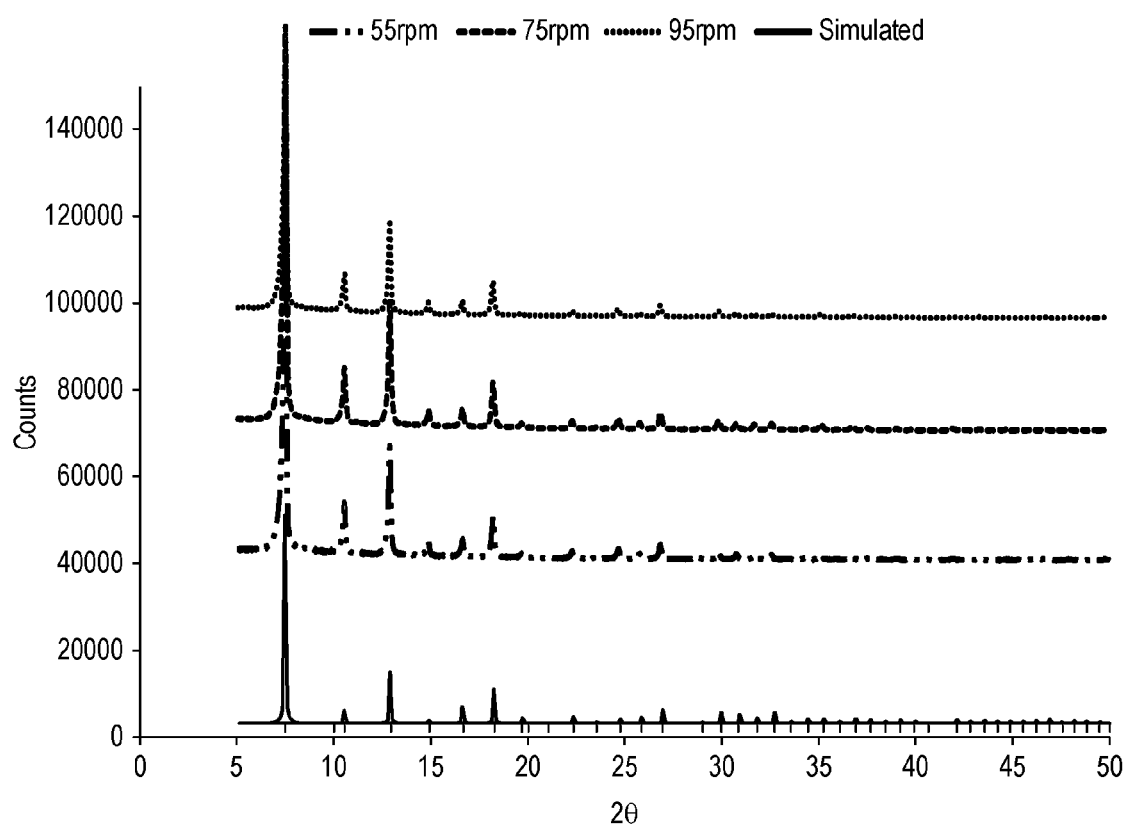
FIG. 6 shows PXRD traces of the activated first extrudates from the extrusions of example 11 at varying speeds (55, 75 and 95 rpm)

Activation was carried out by stirring in HPLC grade methanol (400 mL) at room temperature for 2 hours. The suspension was filtered to obtain a white solid. This was stirred at room temperature in HPLC methanol for a further 2 hours and filtered. The white solid was then dried in an oven at 150° C. for 2 hours. PXRD analysis provided traces matching that of the simulated PXRD pattern of ZIF-8 obtained from the single crystal X-ray diffraction data in the Cambridge Structural Database (FIG. 6). TGA and CHNS analysis also indicated complete reactions at each speed, even after one extrusion.

Example 12—Synthesis of ZIF-8 at 200° C.

Basic zinc carbonate, $[ZnCO_3]_2.[Zn(OH)_2]_3$ (30.81 g, 0.056 moles) and 2-methylimidazole (69.18 g, 0.84 moles) were physically mixed together (Molar ratio 1:15). These were manually fed into the Haake Rheomex OS PTW16, at a screw speed of 95 rpm. The screws consisted mainly of forward conveying sections and two kneading sections. The barrel of the extruder was set at 200° C. A beige molten extrudate was collected from each experiment that solidified quite quickly upon cooling to room temperature. In total 4.5 minutes was required to extrude the reagents and collect the extrudate therefore the throughput rate was determined to be 1.33 kg/hr. Only one extrusion was carried out as previous experiments showed that a complete reaction was obtained after one extrusion. Due to the high temperatures of the experiment, the 2-methylimidazole was observed to have formed a resistant polymer covering the surface of the screws that was difficult to remove.

PXRD of the as-synthesised ZIF-8 was sufficiently similar to the simulated PXRD pattern of ZIF-8 obtained from the single crystal X-ray diffraction data in the Cambridge Structural Database.

Figure 7:
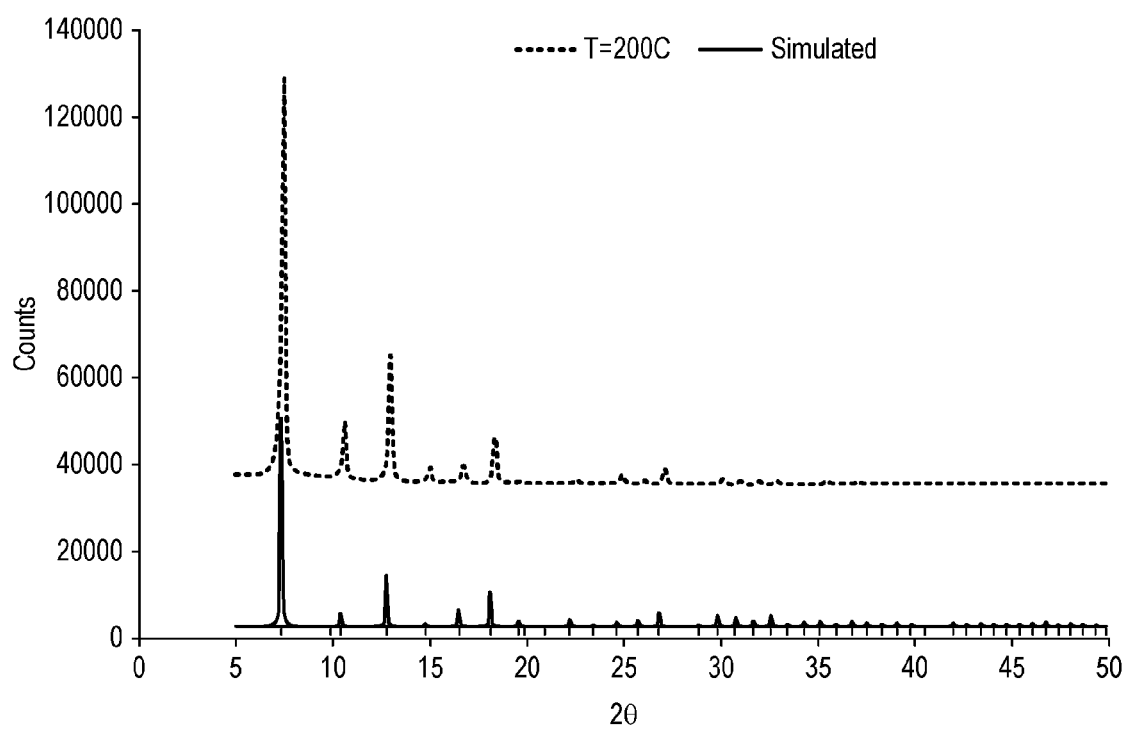
FIG. 7 shows PXRD traces of the activated extrudate from extrusion at 200° C. (55 rpm) (- - -) and the simulated PXRD trace of ZIF-8 from CCDC (-)

Activation was carried out by stirring in HPLC grade methanol (400 mL) at room temperature for 2 hours. The suspension was filtered to obtain a white solid. This was stirred at room temperature in HPLC methanol for a further 2 hours and filtered. The white solid was then dried in an oven at 150° C. for 2 hours. PXRD analysis provided traces matching that of the simulated PXRD pattern of ZIF-8 obtained from the single crystal X-ray diffraction data in the Cambridge Structural Database (FIG. 7).

Example 13—Synthesis of ZIF-8 on the Kilo Scale

Basic zinc carbonate, $[ZnCO_3]_2.[Zn(OH)_2]_3$ (308.1 g, 0.56 moles) and 2-methylimidazole (691.8 g, 8.4 moles) were physically mixed together in one batch (Molar ratio 1:15). This was manually fed into the Haake Rheomex extruder, with a screw speed of 95 rpm. The screws consisted mainly of forward conveying sections and two kneading sections. The barrel of the extruder was set at 200° C. A molten extrudate was produced and it was collected in 5 approximately equal batches to determine homogeneity. The reagents were extruded once only.

PXRD of the as-synthesised extrudates (batches A-E) showed homogeneity and all the traces were very similar to that of the simulated pattern obtained from the single crystal X-Ray structure as provided by the Cambridge Structural Database.

Activation was carried out by stirring a 5 g sample in 40 mL HPLC grade methanol for 2 hours. This was filtered to produce a white powder that was again immersed in solvent and stirred for a further 2 hours. The suspension was filtered and the resulting solid was oven-dried at 150° C. for 2 hours. PXRD of the activated product was very similar to the simulated PXRD trace obtained for ZIF-8 (FIG. 8).

Example 14—Synthesis of $Cu_3(BTC)_2$

Copper (II) hydroxide (0.43 moles, 42.0 g), $Cu(OH)_2$ and benzene-1, 3, 5-tricarboxylic acid (58.0 g, 0.286 moles)

were physically mixed together (Molar ratio 3:2). HPLC grade methanol was added slowly and the mixture was stirred. Heat was produced from the addition of the solvent and the mixed solid became a darker green in colour. These were manually fed into the Haake Rheomex extruder, at a range of screw speeds—55, 75, 95, 115, 135, 155 and 250 rpm. The screws consisted mainly of forward conveying sections and two kneading sections. The barrel of the extruder was kept at room temperature. A light blue extrudate paste was produced which formed large clumps after the first extrusion. These were broke down and a further 20 mL of MeOH was mixed into the extrudate. This was fed through the extruder a second time to produce a blue powder extrudate which was extruded a third time without extra MeOH addition. Throughput rates from the first extrusion were determined and are outlined in Table 3.

TABLE 3

| Screw Speed (rpm) | Throughput Time (mins) | Throughput Rate (kg/hr) |
|---|---|---|
| 55 | 20 | 0.30 |
| 75 | 18 | 0.33 |
| 95 | 14 | 0.43 |
| 115 | 12 | 0.50 |
| 135 | 10 | 0.60 |
| 155 | 9 | 0.66 |
| 250 | 6 | 1.00 |

PXRD of the as-synthesised extrudates indicated a complete reaction as the traces were very similar to that of the simulated trace produced from the single X-Ray crystal structure provided by the Cambridge Structure Database. Complete reactions can be suggested after the first extrusion.

Activation of Extrudates:

Four methods were employed to activate the $Cu_3(BTC)_2$ extrudates.

Method 1: 8 mL of absolute ethanol per 1 g of extrudate was used. The extrudate was immersed in absolute ethanol and sonicated in an ultrasonic cleaning bath for 20 minutes. The suspension was filtered. This process was repeated a further two times and a darkening of the blue colour was observed. The solid product was oven-dried at 150° C. for 2 hours. A dark purple solid was produced.

Method 2: 8 mL of absolute ethanol per 1 g of extrudate was used. The extrudate was immersed in absolute ethanol and stirred for 20 minutes at room temperature. The suspension was then filtered and the process repeated a further two times. Again the darkening of the solid colour can be observed. The solid was oven-dried at 150° C. for 2 hours to produce a dark purple solid.

Method 3: 8 mL of industrial alcohol (99.9% ethanol) per 1 g of extrudate was used. The extrudate was immersed in absolute ethanol and sonicated in an ultrasonic cleaning bath for 20 minutes. The suspension was filtered. This process was repeated a further two times and a darkening of the blue colour was observed. The solid product was oven-dried at 150° C. for 2 hours. A dark purple solid was produced.

Method 4: 8 mL of industrial alcohol (99.9% ethanol) per 1 g of extrudate was used. The extrudate was immersed in absolute ethanol and stirred for 20 minutes at room temperature. The suspension was then filtered and the process repeated a further two times. Again the darkening of the solid colour can be observed. Oven-drying at 150° C. for 2 hours produced a dark purple solid.

PXRDs of these activated products provided traces suitably matching that of the simulated PXRD trace obtained from the Cambridge Structure Database (FIG. 9).

Example 15—Synthesis of $Cu_3(BTC)_2$ (Varying Methanol % Wt)

Copper (II) hydroxide (0.43 moles, 42.0 g), $Cu(OH)_2$ and benzene-1, 3, 5-tricarboxylic acid (58.0 g, 0.286 moles) were physically mixed together (Molar ratio 3:2). Varying amounts of HPLC grade methanol (40 mL, 60 mL, 80 mL, 100 mL and 120 mL) were added slowly in each experiment and the mixture was stirred. Heat was produced from the addition of the solvent and the mixed solid became a darker green in colour for the mixtures in which more than 60 mL of methanol was added. These were manually fed into the Haake Rheomex extruder, with a screw of length:diameter ratio of 25 twin screw extruder at 135 rpm. The screws consisted mainly of forward conveying sections and two kneading sections. The barrel of the extruder was kept at room temperature. A light blue powder extrudate was produced except for the experiment with 40 mL of methanol which produced a green extrudate. PXRD of the as-synthesised extrudates suggest complete reaction upon addition of 60-120 mL methanol. The PXRD of the experiment employing 40 mL of methanol showed the presence of $Cu(OH)_2$ and was therefore unsuccessful. Activation was carried out via Method 2 outlined above to produce dark purple powders from the experiments involving 60 mL or more of solvent. PXRD of the activated products were sufficiently similar to the simulated PXRD trace provided by the Cambridge Structure Database.

Example 16—Synthesis of $Cu_3(BTC)_2$ (Varying Industrial Alcohol % Wt)

Copper (II) hydroxide (0.43 moles, 42.0 g), $Cu(OH)_2$ and benzene-1, 3, 5-tricarboxylic acid (58.0 g, 0.286 moles) were physically mixed together (Molar ratio 3:2). Varying amounts of industrial alcohol (99.9% ethanol) (40 mL, 60 mL, 80 mL, 100 mL and 120 mL) were added slowly in each experiment and the mixture was stirred. Heat was produced from the addition of the solvent and the mixed solid became a darker green in colour for the mixtures in which more than 60 mL of industrial alcohol was added. These were manually fed into the ThermoFisher Process 11, at a screw speed of 135 rpm. The screws consisted mainly of forward conveying sections and two kneading sections. The barrel of the extruder was kept at room temperature. A light blue powder extrudate was produced, however the experiment employing 40 mL of industrial alcohol produced a green extrudate.

PXRD of the as-synthesised extrudates suggest complete reaction upon addition of 60-120 mL industrial alcohol. The PXRD of the experiment employing 40 mL of industrial alcohol showed the presence of $Cu(OH)_2$ and was therefore unsuccessful.

Activation was carried out via Method 4 outlined above to produce dark purple powders from the experiments involving 60 mL or more of solvent. PXRD of the activated products were sufficiently similar to the simulated PXRD trace provided by the Cambridge Structure Database.

Example 17—Synthesis of $Cu_3(BTC)_2$ on the Kilo Scale

Copper (II) hydroxide (4.30 moles, 420.0 g), $Cu(OH)_2$ and benzene-1, 3, 5-tricarboxylic acid (580.0 g, 0.2.86 moles) were physically mixed together (Molar ratio 3:2). 400 mL of methanol was added slowly to the reagent mixture, heat was produced from the addition of the solvent and the mixed solid became a darker green in colour. This was manually fed into the Haake Rheomex extruder, at a screw speed of 135 rpm. The screws consisted mainly of forward conveying sections and two kneading sections. The barrel of the extruder was kept at room temperature. A light blue powder extrudate was produced and collected in 5 batches to check for homogeneity. PXRD of the as-synthesised extrudates (batches A-E) showed homogeneity and all the traces were very similar to that of the simulated pattern obtained from the single crystal X-Ray structure as provided by the Cambridge Structural Database.

Activation of 50 g was carried out via Method 2 to produce a dark purple solid after oven-drying at 150° C. for 2 hours. PXRD of the activated product produced a trace that was matching to the simulated trace obtained from the Cambridge Structure Database (FIG. 10).

Example 18—Synthesis of $Cu_3(BTC)_2$ with Reduced Residence Times

Copper (II) hydroxide (0.43 moles, 42.0 g), $Cu(OH)_2$ and benzene-1, 3, 5-tricarboxylic acid (58.0 g, 0.286 moles) were physically mixed together (Molar ratio 3:2). Industrial alcohol (99.9% ethanol), 80 mL, was added slowly and the mixture was stirred. Heat was produced from the addition of the solvent and the mixed solid became a darker green in colour. These were manually fed into the ThermoFisher Process 11 Parallel Twin Screw Extruder, with a screw speed of 155 and 250 rpm. The screws consisted mainly of forward conveying sections and only one kneading section. The residence time was measured to be ca. 12 seconds at 155 rpm and ca. 6 seconds at 250 rpm. The barrel of the extruder was kept at room temperature. A light blue extrudate powder was produced. PXRD of the as-synthesised extrudates suggest a complete reaction in both cases as the traces are very similar to the simulated trace produced by the Cambridge Structure Database. Activation was carried out via Method 4 to produce dark purple powders in both cases. PXRD of the activated products were sufficiently similar to the simulated PXRD trace provided by the Cambridge Structure Database (FIG. 11).

Example 19—Synthesis of $Cu_3(BTC)_2$ with Reduced Residence Times

Copper (II) hydroxide (0.43 moles, 42.0 g), $Cu(OH)_2$ and benzene-1, 3, 5-tricarboxylic acid (58.0 g, 0.286 moles) were physically mixed together (Molar ratio 3:2). Industrial alcohol (99.9% ethanol), 80 mL, was added slowly and the mixture was stirred. Heat was produced from the addition of the solvent and the mixed solid became a darker green in colour. These were manually fed into a ThemoFisher Process 11 Extruder, with a screw speed of 155 and 250 rpm. The mixture was fed into the last conveying section of the screw. The residence time was measured to be ca. 3-4 seconds at 155 rpm and ca. 1-2 seconds at 250 rpm. The barrel of the extruder was kept at room temperature. A light blue extrudate powder was produced. PXRD of the as-synthesised extrudates suggest a complete reaction in both cases as the traces are very similar to the simulated trace produced by the Cambridge Structure Database. Activation was carried out via Activation Method 4 to produce dark purple powders in both cases. PXRD of the activated products were sufficiently similar to the simulated PXRD trace provided by the Cambridge Structure Database (FIG. 12).

Example 21—Synthesis of Alq.AcOH

Basic aluminium diacetate (8.1 g, 0.049 moles) and 8-hydroxyquinoline (22.65 g, 0.156 moles) were physically mixed together (Molar ratio 1:3). These were manually fed into a ThermoFisher Process 11 Extruder, at a screw speed of 55 rpm (residence time ca. 1.5-2 minutes). A dark yellow solid was produced. PXRD of the as-synthesised extrudate suggest a complete reaction in both cases as the traces are very similar to the simulated trace produced by the Cambridge Structure Database (FIG. 13). Excess acetic acid could be removed via heating at 200° C. for 2.0 hours to produce a bright yellow solid.

Example 22—Synthesis of $[Ni(NCS)_2(PPh_3)_2]$

Nickel (II) thiocyanate (5 g, 0.028 moles) and triphenylphosphine (15 g, 0.0572 moles) were physically mixed together (Molar ratio 1:2). To this, 0.4 equivalents of HPLC grade methanol was added (0.0112 moles, 0.57 mL). This paste was manually fed into a ThermoFisher Process 11 Extruder, at a screw speed of 55 rpm (residence time ca. 1.5-2 minutes). An orange solid was produced. PXRD of the as-synthesised extrudate suggest a complete reaction in both cases as the traces are very similar to the simulated trace produced by the Cambridge Structure Database (FIG. 14).

Example 23—Synthesis of [Ni(Salen)]

Nickel (II) acetate tetrahydrate (9.27 g, 0.037 moles) and $salenH_2$ (2,2'-[1,2-Ethanediylbis[(E)-nitrilomethylidyne]] bis-phenol) (10 g, 0.037 moles) were physically mixed together (Molar ratio 1:1). To this 0.3 equivalents of HPLC grade methanol was added (0.0111, 0.449 mL). This paste was manually fed into the ThermoFisher Process 11 Extruder, with a screw speed of 55 rpm (residence time ca. 1.5-2 minutes). A brick red solid was produced. PXRD of the as-synthesised extrudate suggest a complete reaction in both cases as the traces are very similar to the simulated trace produced by the Cambridge Structure Database (FIG. 15).

Example 24—Synthesis of ZIF-8 on the Kilo Scale Via Single Screw Extrusion

Basic zinc carbonate, $[ZnCO_3]_2.[Zn(OH)_2]_3$ (308.1 g, 0.56 moles) and 2-methylimidazole (691.8 g, 8.4 moles) were physically mixed together in one batch (Molar ratio 1:15). This was manually fed into a Dr. Collin E 25M single screw extruder with a l/d ratio of 25 at a speed of 30 rpm. A 25 mm diameter PTFE screw of constantly increasing root diameter was used. The screw consisted essentially of a conveying section and a short kneading section in the final zone. FIG. 16 shows the PTFE screw used in the experiment, highlighting the constantly increasing root diameter (top image) and the kneading section (bottom image). There were 5 zones making up the barrel, each set at different temperatures, Zone 1 i.e. the feeding zone was kept at 30° C. Zone 2 was kept at 50° C., Zone 3 at 130° C. and the final two zones at 150° C. The product emerged from the extruder as a beige solid suspended in the excess liquid 2-methylimidazole. This solidified upon cooling. The product was collected as one batch. The reagents were extruded once only. Several PXRD patterns of the as-synthesised extrudate were determined and showed homogeneity within the batch. All the traces were very similar to that of the simulated pattern of ZIF-8 obtained from the Cambridge Crystallographic Data Centre (FAWCEN), there were some differences between them and the simulated powder pattern for ZIF-8, but this was as a result of the excess 2-methylimidazole being occluded in the pores of the resulting MOF.

Activation was carried out by stirring a 5 g sample in 40 mL HPLC grade methanol for 2 hours. This was filtered to produce a white powder that was again immersed in solvent and stirred for a further 2 hours. The suspension was filtered and the resulting solid was oven-dried at 150° C. for 2 hours. PXRD of the activated product was very similar to the simulated PXRD trace obtained for ZIF-8 (FIG. 17).

The invention claimed is:

1. A process for the preparation of a metal-organic compound, said metal-organic compound comprising at least one metal ion and at least one organic ligand, wherein said organic ligand is capable of associating with said metal ion, the process comprising:
   a. providing a first reactant comprising at least one metal in ionic form, wherein the metal is selected from Zn, Co, Mg, Cu, Al, a lanthanide, Fe, Li, Sc, Mn, Cr, Ti, Zr, Ni, and combinations thereof;
   b. providing a second reactant comprising at least one organic ligand capable of associating with said metal in ionic form, wherein the second reactant is an imidazole, pyridine, or carboxylic acid, moiety; and
   c. admixing said first and second reactants under conditions of prolonged and sustained pressure and shear sufficient to synthesise said metal-organic compound.

2. The process as claimed in claim 1, wherein said pressure and shear are applied by an extrusion process.

3. The process of claim 2, wherein the extrusion process is a screw-based extrusion process.

4. The process of claim 3, wherein the screw-based process is a multiple screw-based extrusion process.

5. The process of claim 4, wherein the screw-based extrusion process is a twin-screw extrusion process.

6. The process of claim 5, wherein the twin-screw extrusion process is a co-rotating twin-screw extrusion process or a counter-rotating twin-screw extrusion process.

7. The process of claim 3, wherein the screws are at least partially intermeshing.

8. The process as claimed in claim 1, wherein at least one of the first reactant and the second reactant in steps (a) and (b) is dry.

9. The process as claimed in claim 1, wherein the mixing of the reactants in step (c) is dry-mixing.

10. The process as claimed in claim 1, wherein the mixing of the reactants together is carried out in an extruder in the absence of an added solvent.

11. The process as claimed in claim 1, wherein the process is carried out in the presence of a liquid.

12. The process as claimed in claim 11, wherein the liquid is a solvent.

13. The process of claim 12, wherein said solvent is a hydrocarbon, an alcohol, water, an amide, an amine, an ester, an ionic liquid, a carboxylic acid, a base, an ether, a halogenated solvent, an aromatic solvent a sulfoxide or any combination of such solvents.

14. The process as claimed in claim 1, wherein the first reactant is a salt, or in salt form, including an oxide.

15. The process as claimed in claim 14, wherein the first reactant is a metal nitrate, nitrite, oxide, hydroxide, alkoxide, aryloxide, carbonate, sulfate, acetate, formate, benzoate, acetylacetonate, fluoride, chloride, bromide, iodide, or tartrate, hydrogen carbonate, phosphate, hydrogen phosphate, dihydrogen phosphate or sulfonate.

16. The process as claimed in claim 1, wherein the first and second reactants are exposed to additional heat during step (c).

17. The process as claimed in claim 16, wherein said first and second reactants are exposed to a temperature within 20° C. of the melting point of one of the first and second reactants.

18. The process as claimed in claim 1, wherein the process is a continuous process.

19. The process as claimed in claim 2, wherein the first and second reactants are mixed prior to passing into the extruder.

20. The process as claimed in claim 1, further providing step (d) heating the so-formed metal-organic compound in a subsequent heating step.

21. The process as claimed in claim 20, wherein said heating step involves a temperature change of up to 250° C.

22. The process as claimed in claim 1, wherein the process includes more than two reactants to obtain a multi-metal and/or multi-bridging-substance 2D or 3D metal-organic compound.

23. The process as claimed in claim 1, where the second reactant is selected from the group consisting of 2-methyl imidazole; 2-ethylimidazole; benzimidazole; trans-1,4-butene dicarboxylic acid (fumaric acid); 2-methyl imidazole; Isonicotinic acid; 1,4-benzenedicarboxylic acid (terephthalic acid); 1,3,5-benzenetricarboxylic acid; 2,5-dihydroxybenzene 1,4-dicarboxylic acid (2,5-dihydroxyterephthalic acid); 4,4'-bipyridine; 1,3 benzene dicarboxylic acid; and 4,4'-biphenyldicarboxylic acid.

* * * * *